US011786518B2

(12) United States Patent
Clark et al.

(10) Patent No.: US 11,786,518 B2
(45) Date of Patent: *Oct. 17, 2023

(54) OPHTHALMIC FORMULATIONS AND USES THEREOF

(71) Applicant: Aldeyra Therapeutics, Inc., Lexington, MA (US)

(72) Inventors: David Clark, Winchester, MA (US); Susan Macdonald, Danvers, MA (US); Stephen Gitu Machatha, Wilmington, MA (US); Lise Lund Kjems, Concord, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 446 days.

This patent is subject to a terminal disclaimer.

(21) Appl. No.: 16/825,898

(22) Filed: Mar. 20, 2020

(65) Prior Publication Data

US 2020/0323841 A1 Oct. 15, 2020

Related U.S. Application Data

(60) Provisional application No. 62/857,874, filed on Jun. 6, 2019, provisional application No. 62/824,233, filed on Mar. 26, 2019.

(51) Int. Cl.
*A61K 31/47* (2006.01)
*A61K 47/40* (2006.01)
*A61P 27/14* (2006.01)
*A61K 9/08* (2006.01)
*A61K 9/00* (2006.01)

(52) U.S. Cl.
CPC ............ *A61K 31/47* (2013.01); *A61K 9/0048* (2013.01); *A61K 9/08* (2013.01); *A61K 47/40* (2013.01); *A61P 27/14* (2018.01)

(58) Field of Classification Search
None
See application file for complete search history.

(56) References Cited

U.S. PATENT DOCUMENTS

| | | | |
|---|---|---|---|
| 3,912,748 A | 10/1975 | Evans et al. | |
| 4,668,626 A | 5/1987 | Kobayashi et al. | |
| 4,956,351 A | 9/1990 | Mesens et al. | |
| 5,024,998 A | 6/1991 | Bodor | |
| 5,032,392 A | 7/1991 | Varma | |
| 5,364,637 A | 11/1994 | De et al. | |
| 5,376,645 A | 12/1994 | Stella et al. | |
| 5,419,898 A | 5/1995 | Ikejiri et al. | |
| 5,472,954 A | 12/1995 | Loftsson | |
| 5,576,311 A | 11/1996 | Guy | |
| 5,668,117 A | 9/1997 | Shapiro | |
| 5,767,109 A | 6/1998 | Sanchez et al. | |
| 5,998,488 A | 12/1999 | Shinohara et al. | |
| 6,191,127 B1 | 2/2001 | Holscher et al. | |
| 6,444,221 B1 | 9/2002 | Shapiro | |
| 6,492,520 B1 | 12/2002 | Chen | |
| 6,525,056 B2 | 2/2003 | Arvanitis et al. | |
| 7,973,025 B2 | 7/2011 | Jordan et al. | |
| 7,982,071 B2 | 7/2011 | Scott et al. | |
| 8,158,609 B1 | 4/2012 | Marsh et al. | |
| 8,435,965 B2 | 5/2013 | Tabuchi et al. | |
| 8,722,669 B2 | 5/2014 | Palczewski et al. | |
| 8,791,154 B2 | 7/2014 | Gamache et al. | |
| 8,940,721 B2 | 1/2015 | Jordan et al. | |
| 8,940,764 B2 | 1/2015 | Jordan et al. | |
| 9,265,759 B2 | 2/2016 | Jordan et al. | |
| 9,364,471 B2 | 6/2016 | Jordan et al. | |
| 9,604,997 B2 | 3/2017 | Jordan et al. | |
| 9,650,342 B2 | 5/2017 | Jordan et al. | |
| 9,687,481 B2* | 6/2017 | Brady | A61P 17/02 |
| 9,814,701 B2 | 11/2017 | Jordan et al. | |
| 9,896,419 B2 | 2/2018 | Jordan et al. | |
| 10,111,862 B2 | 10/2018 | Chabala et al. | |
| 10,202,348 B2 | 2/2019 | Jordan et al. | |
| 10,213,395 B2 | 2/2019 | Brady et al. | |
| 10,414,732 B2 | 9/2019 | Buist et al. | |
| 10,426,790 B2 | 10/2019 | Young et al. | |
| 10,543,181 B2 | 1/2020 | Brady et al. | |
| 10,550,085 B2 | 2/2020 | Brady et al. | |
| 10,588,874 B2 | 3/2020 | Brady et al. | |
| 10,913,722 B2 | 2/2021 | Jordan et al. | |
| 11,007,157 B2 | 5/2021 | Brady et al. | |
| 11,040,039 B2 | 6/2021 | Macdonald et al. | |
| 11,046,650 B2 | 6/2021 | Brady et al. | |
| 11,129,823 B2 | 9/2021 | Brady et al. | |
| 11,197,821 B2* | 12/2021 | Clark | A61K 47/40 |

(Continued)

FOREIGN PATENT DOCUMENTS

| CN | 101321742 A | 12/2008 |
|---|---|---|
| CN | 104884049 A | 9/2015 |

(Continued)

OTHER PUBLICATIONS

Winfield, Ophthalmic products (Tonicity, pH adjustment), Pharmaceutical Practice, Churchill Livingstone, 2004, 265-268.*
Abelson et al., "Combined analysis of two studies using the conjunctival allergen challenge model to evaluate olopatadine hydrochloride, a new ophthalmic antiallergic agent with dual activity," American Journal of Ophthalmology, 125(6):797-804 (Jun. 1998).
Abelson et al., "Conjunctival allergen challenge. A clinical approach to studying allergic conjunctivitis," Archives of Ophthalmology, 108(1):84-88 (1990).
Abelson et al., "Conjunctival allergen challenge: models in the investigation of ocular allergy," Current Allergy and Asthma Reports, 3(4):363-368 (2003).

(Continued)

*Primary Examiner* — Gigi G Huang
(74) *Attorney, Agent, or Firm* — Dechert LLP; Andrea L. C. Reid; Kiruthika Elamparuthi

(57) ABSTRACT

The present invention provides a reproxalap ophthalmic solution, and methods of using the same for treating a disease or disorder such as allergic conjunctivitis.

23 Claims, 5 Drawing Sheets

(56) References Cited

U.S. PATENT DOCUMENTS

| | | |
|---|---|---|
| 11,312,692 B1 | 4/2022 | Machatha et al. |
| 2004/0198828 A1 | 10/2004 | Abelson et al. |
| 2005/0090553 A1 | 4/2005 | Shapiro |
| 2005/0130906 A1 | 6/2005 | Matier et al. |
| 2005/0234018 A1 | 10/2005 | Lyons et al. |
| 2006/0111318 A1 | 5/2006 | Okamoto |
| 2006/0257488 A1 | 11/2006 | Hubbard |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2009/0182009 A1 | 7/2009 | Jordan et al. |
| 2010/0240624 A1 | 9/2010 | Chapin et al. |
| 2011/0105450 A1 | 5/2011 | Chapin et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1* | 11/2012 | Jordan .................... A61K 47/40 514/375 |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2015/0209333 A1 | 7/2015 | Jordan et al. |
| 2015/0209345 A1 | 7/2015 | Jordan et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0168098 A1 | 6/2016 | Jordan et al. |
| 2017/0095449 A1 | 4/2017 | Winters et al. |
| 2017/0239196 A1 | 8/2017 | Brady et al. |
| 2017/0266220 A1* | 9/2017 | Young .................... A61P 27/02 |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0105322 A1 | 4/2019 | Macdonald et al. |
| 2019/0125729 A1 | 5/2019 | Chabala et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |
| 2021/0269402 A1 | 9/2021 | Jordan et al. |
| 2021/0275469 A1 | 9/2021 | Brady et al. |
| 2021/0347735 A1 | 11/2021 | Brady et al. |
| 2021/0353628 A1 | 11/2021 | Macdonald et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |
| 2022/0184057 A1 | 6/2022 | Brady et al. |
| 2022/0202745 A1 | 6/2022 | Brady et al. |
| 2022/0211691 A1 | 7/2022 | Brady et al. |

FOREIGN PATENT DOCUMENTS

| | | |
|---|---|---|
| EP | 2301549 A1 | 3/2011 |
| EP | 1888548 B1 | 8/2012 |
| JP | 06-239748 A | 8/1994 |
| JP | 07-025758 A | 1/1995 |
| JP | 09-169647 A | 6/1997 |
| JP | 2001041757 A | 6/2001 |
| JP | 2002003364 A | 1/2002 |
| JP | 2002003364 A | 1/2002 |
| JP | 2002003364 T | 1/2002 |
| JP | 2005-132834 A | 5/2005 |
| JP | 2005-187407 A | 7/2005 |
| JP | 2006-008568 A | 1/2006 |
| JP | 3736916 B2 | 1/2006 |
| JP | 2007532648 A | 11/2007 |
| JP | 4466875 B2 | 5/2010 |
| JP | 4466875 B2 | 5/2010 |
| JP | 4466875 T | 5/2010 |
| JP | 4748289 B2 | 8/2011 |
| JP | 2012506449 A | 3/2012 |
| JP | 5194218 B2 | 5/2013 |
| JP | 5194218 B2 | 5/2013 |
| JP | 5194218 T | 5/2013 |
| JP | 2014-515355 A | 6/2014 |
| JP | 2015-057437 A | 3/2015 |
| JP | 2015-535293 A | 12/2015 |
| WO | 2001041757 A1 | 6/2001 |
| WO | WO-2005105067 A2 | 11/2005 |
| WO | WO-2006000421 A2 | 1/2006 |
| WO | WO-2006002473 A1 | 1/2006 |
| WO | WO-2006127945 A1 | 11/2006 |
| WO | 2010048332 A2 | 4/2010 |
| WO | WO-2011008202 A1 | 1/2011 |
| WO | WO-2011071995 A2 | 6/2011 |
| WO | WO-2011072141 A1 | 6/2011 |
| WO | WO-2012105887 A1 | 8/2012 |
| WO | WO-2014100425 A1 | 6/2014 |
| WO | WO-2014116593 A1 | 7/2014 |
| WO | WO-2014116836 A2 | 7/2014 |
| WO | WO-2015002893 A1 | 1/2015 |
| WO | WO-2015187942 A1 | 12/2015 |
| WO | WO-2016085939 A2 | 6/2016 |
| WO | WO-2017035077 A1 | 3/2017 |
| WO | WO-2017035082 A1 | 3/2017 |
| WO | WO-2017147617 A1 | 8/2017 |
| WO | WO-2017196881 A1* | 11/2017 ........... A61K 31/165 |
| WO | WO-2018039192 A1 | 3/2018 |
| WO | WO-2018039197 A1 | 3/2018 |
| WO | WO-2018064354 A1 | 4/2018 |
| WO | WO-2018170476 A1 | 9/2018 |
| WO | WO-2019075136 A1 | 4/2019 |
| WO | WO-2020018498 A1 | 1/2020 |
| WO | WO-2020028820 A1 | 2/2020 |
| WO | WO-2020033344 A1 | 2/2020 |
| WO | WO-2020068986 A1 | 4/2020 |
| WO | WO-2020072621 A1 | 4/2020 |
| WO | WO-2020118045 A1 | 6/2020 |
| WO | 2021195211 A1 | 9/2021 |
| WO | 2021211625 A1 | 10/2021 |
| WO | 2021248031 A1 | 12/2021 |

OTHER PUBLICATIONS

Abelson et al., The conjunctival provocation test model of ocular allergy: utility for assessment of an ocular corticosteroid, loteprednol etabonate, J Ocul Pharmacol Ther, 14(6):533-42 (Dec. 1998).

Ackerman et al., "Ocular itch associated with allergic conjunctivitis: latest evidence and clinical management," Ther. Adv. Chronic Dis., 2016; 7(1):52-67.

Aldeyra Press Release—Aldeyra Therapeutics Abstract Accepted at 2015 American Academy of Allergy Asthma & Immunology Annual Meeting, Dec. 16, 2014 (2 pages).

Aldeyra Press Release—Aldeyra Therapeutics Abstracts Accepted for Presentation at the 2015 Annual Meeting of the Association for Research in Vision and Ophthalmology, Feb. 2, 2015 (2 pages).

Aldeyra Press Release—Aldeyra Therapeutics Announces Clinical Development Update for Phase 3 Programs, Jan. 25, 2017 (2 pages).

Aldeyra Press Release—Aldeyra Therapeutics Announces First Patient Enrolled in Allergic Conjunctivitis Phase 2b Clinical Trial, Feb. 7, 2017 (2 pages).

Aldeyra Press Release—Aldeyra Therapeutics Announces First Patient Enrolled in Allergic Conjunctivitis Phase 3 Clinical Trial, Apr. 24, 2018 (2 pages).

Aldeyra Press Release—Aldeyra Therapeutics Announces First Patient Enrolled in Allergic Conjunctivitis Phase 3 Clinical Trial, May 1, 2018 (2 pages).

(56) References Cited

OTHER PUBLICATIONS

Aldeyra Press Release—Aldeyra Therapeutics Announces First Patient Enrolled in Allergic Conjunctivitis Phase IIa Clinical Trial, Sep. 29, 2015 (2 pages).
Aldeyra Press Release—Aldeyra Therapeutics Announces First Patient Enrolled in Dry Eye Disease Phase 2a Clinical Trial, Jun. 6, 2017 (2 pages).
Aldeyra Press Release—Aldeyra Therapeutics Announces First Patient Enrolled in Dry Eye Disease Phase 2b Clinical Trial, Jan. 30, 2018 (2 pages).
Aldeyra Press Release—Aldeyra Therapeutics Announces First Patient Enrolled in Noninfectious Anterior Uveitis Phase 3 Clinical Trial, Apr. 27, 2017 (2 pages).
Aldeyra Press Release—Aldeyra Therapeutics Announces First Patient Enrolled in Noninfectious Anterior Uveitis Phase II Clinical Trial, Apr. 16, 2015 (2 pages).
Aldeyra Press Release—Aldeyra Therapeutics Announces Last Patient Dosed in Dry Eye Disease Phase 2a Clinical Trial, Jul. 18, 2017 (2 pages).
Aldeyra Press Release—Aldeyra Therapeutics Announces Last Patient Dosed in Dry Eye Disease Phase 2b Clinical Trial, Jul. 12, 2018 (2 pages).
Aldeyra Press Release—Aldeyra Therapeutics Announces Last Patient Dosed in Phase II Trial of NS2 in Patients with Allergic Conjunctivitis, Dec. 16, 2015 (2 pages).
Aldeyra Press Release—Aldeyra Therapeutics Announces Last Patient Dosed in the Alleviate Phase 3 Clinical Trial, Dec. 20, 2018 (2 pages).
Aldeyra Press Release—Aldeyra Therapeutics Announces Positive Results from Phase 2b Dry Eye Disease Clinical Trial, Sep. 26, 2018 (2 pages).
Aldeyra Press Release—Aldeyra Therapeutics Announces Positive Top-Line Results from the Phase 3 Alleviate Trial in Patients with Allergic Conjunctivitis, Mar. 26, 2019 (2 pages).
Aldeyra Press Release—Aldeyra Therapeutics Announces Presentation of Phase 2 Allergic Conjunctivitis Results at the 2016 American College of Allergy, Asthma and Immunology Annual Scientific Meeting, Nov. 7, 2016 (2 pages).
Aldeyra Press Release—Aldeyra Therapeutics Announces Presentation of Results on the Efficacy of ADX-102 in Noninfectious Anterior Uveitis at the American Uveitis Society Held at the American Academy of Ophthalmology 2017 Annual Meeting, Oct. 25, 2017 (2 pages).
Aldeyra Press Release—Aldeyra Therapeutics Announces Results from Allergic Conjunctivitis Phase 2b Clinical Trial and Plans for Phase 3 Clinical Testing, Jun. 14, 2017 (3 pages).
Aldeyra Press Release—Aldeyra Therapeutics Announces Third Quarter 2017 Financial Results, Nov. 9, 2017 (4 pages).
Aldeyra Press Release—Aldeyra Therapeutics Opens Enrollment in Noninfectious Anterior Uveitis Phase II Clinical Trial, Mar. 26, 2015 (2 pages).
Aldeyra Press Release—Aldeyra Therapeutics Opens Enrollment in Sjogren-Larsson Syndrome Clinical Trial and Finalizes Noninfectious Anterior Uveitis Clinical Trial Protocol, Mar. 17, 2015 (2 pages).
Aldeyra Press Release—Aldeyra Therapeutics Presents Noninfectious Anterior Uveitis Phase 2 Clinical Trial Data at the Association for Research in Vision and Ophthalmology 2017 Annual Meeting, May 17, 2017 (3 pages).
Aldeyra Press Release—Aldeyra Therapeutics Presents Noninfectious Anterior Uveitis Phase 2 Clinical Trial Data to the American Uveitis Society Held at the American Academy of Ophthalmology 2017 Annual Meeting, Nov. 29, 2017 (2 pages).
Aldeyra Press Release—Aldeyra Therapeutics Provides Update on Late-Stage Clinical Trials at 2016 Research and Development Day, Sep. 26, 2016 (2 pages).
Aldeyra Press Release—Aldeyra Therapeutics Provides Update on NS2 Clinical Program, Mar. 2, 2015 (2 pages).
Aldeyra Press Release—Aldeyra Therapeutics Provides Update on Ophthalmic Programs at 2019 Research & Development Day, Feb. 28, 2019 (2 pages).
Aldeyra Press Release—Aldeyra Therapeutics Reaches Agreement with the US Food and Drug Administration for the Use of RASP as an Objective Sign for the Treatment of Dry Eye Disease, Jun. 4, 2020 (2 pages).
Aldeyra Press Release—Aldeyra Therapeutics Schedules Conference Call and Webcast to Announce Results from Allergic Conjunctivitis Phase 2b Clinical Trial, Jun. 13, 2017 (1 page).
Aldeyra Press Release—Aldeyra Therapeutics Schedules Webcast and Conference Call to Announce Results from Dry Eye Disease Phase 2a Clinical Trial, Sep. 11, 2017 (1 page).
Aldeyra Press Release—Aldeyra Therapeutics Schedules Webcast and Conference Call to Announce Results from Dry Eye Disease Phase 2a Clinical Trial, Sep. 12, 2017 (3 pages).
Aldeyra Press Release—Aldeyra Therapeutics Selected for Podium Presentation of Phase 2a Dry Eye Disease Results at the 2018 Association for Research in Vision and Ophthalmology (ARVO) Annual Meeting, Feb. 21, 2018 (3 pages).
Aldeyra Press Release—Aldeyra Therapeutics Submits FDA IND Filing for Noninfectious Anterior Uveitis, Dec. 18, 2014 (2 pages).
Aldeyra Press Release—Aldeyra Therapeutics to Host 2019 Research & Development Day, Feb. 12, 2019 (1 page).
Aldeyra Press Release—Aldeyra Therapeutics' Data on Lead Candidate NS2 to be Presented at Society for Investigative Dermatology 2014 Annual Meeting, May 8, 2014 (2 pages).
Aldeyra Press Release—Aldeyra Therapeutics, Inc. Announces Last Patient Dosed in Allergic Conjunctivitis Phase 2b Clinical Trial, Apr. 18, 2017 (2 pages).
Aldeyra Press Release—Positive Results From Phase II Clinical Trial in Subjects With Noninfectious Anterior Uveitis, May 9, 2016 (4 pages).
Aldeyra Press Release—Phase II Allergic Conjunctivitis, Feb. 29, 2016 (3 pages).
Aldini et al., "Lipoxidation-Derived Reactive Carbonyl Species as Potential Drug Targets in Preventing Protein Carbonylation and Related Cellular Dysfunction," ChemMedChem, 1(10):1045-1058 (2006).
Amara et al., "Autoantibodies to malondialdehyde-modified epitope in connective tissue disease and vasculitides," Clinical and Experimental Immunology, 101(2):233-238 (1995).
Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 39(6):1029-1034 (2016).
Augustin et al., "Oxidative reactions in the tear fluid of patients suffering from dry eyes," Graefe's Archive for Clinical and Experimental Ophthalmology, 233(11):694-698 (1995).
Bacsi et al., "Effect of pollen-mediated oxidative stress on immediate hypersensitivity reactions and late-phase inflammation in allergic conjunctivitis," J. Allergy Clin. Immunol., 2005; 116(4):836-843.
Badii, "Allergic Conjunctivitis," https://www.healthline.com/health/allergic-conjunctivitis, Apr. 28, 2016 (12 pages) [retrieved on Nov. 22, 2019].
Balci et al., "Effects of computer monitor-emitted radiation on oxidant/antioxidant balance in cornea and lens from rats," Molec Vis, 15:2521-2525 (2009).
Balci et al., "Investigation of oxidative stress in pterygium tissue," Molecular Vision, 17:443-447 (Feb. 2011).
Baltatzis et al., "Mycophenolate mofetil as an immunomodulatory agent in the treatment of chronic ocular inflammatory disorders," Ophthalmology, 110(5):1061-5 (May 2003).
Boldogh et al., "ROS generated by pollen NADPH oxidase provide a signal that augments antigen-induced allergic airway inflammation," J. Clin. Invest., 2005; 115(8):2169-2179.
Boyer et al., "Lipofuscin and N-Retinylidene-N-Retinylethanolamine (A2E) Accumulate in Retinal Pigment Epithelium in Absence of Light Exposure," J Biol Chem, 287(26):22276-22286 (Jun. 2012).
Bozkir et al., "Effect of hydroxypropyl-beta-cyclodextrin on the solubility, stability and in-vitro release of ciprofloxacin for ocular drug delivery," Acta Poloniae Pharmaceutica, 69(4):719-24 (2012).

(56) References Cited

OTHER PUBLICATIONS

Bragagni et al., "Cyclodextrin complexation highly enhances efficacy of arylsulfonylureido benzenesulfonamide carbonic anhydrase inhibitors as atopical antiglaucoma agents," Bioorganic & Medicinal Chemistry, 23(18):6223-6227 (2015).
Brewitt et al., "Dry Eye Disease—The Scale of the Problem," Survey of Ophthalmol, 45(Suppl 2):S199-S2 (Mar. 2001).
Bridion® (sugammadex) Injection Prescribing Information, for intravenous use, Initial U.S. Approval: 2015, Last Revised Dec. 2015 (19 pages).
Brozek et al., "Grading quality of evidence and strength of recommendations in clinical practice guidelines: Part 2 of 3. The GRADE approach to grading quality of evidence about diagonstic tests and strategies," Allergy, 64(8):1109-1116 (2009).
Buddi et al., "Evidence of oxidative stress in human corneal diseases," The Journal of Histochemistry and Cytochemistry: official journal of the Histochemistry Society, 50(3):341-351 (2002).
Burcham et al., "Aldehyde-Sequestering Drugs: Tools for Studying Protein Damage by Lipid Peroxidation Products," Toxicology, 181-182:229-236 (2002).
Burstein, "Preservative cytotoxic threshold for benzalkonium chloride and chlorhexidine digluconate in cat and rabbit corneas," Investigative Ophthalmology and Visual Science, 19(3):308-313 (1980).
Burstein, "The effects of topical drugs and preservatives on the tears and corneal epithelium in dry eye," Transactions of the Ophthalmological Societies of the United Kingdom, 104:402-409 (1985).
Canonica et al., "Recommendations for standardization of clinical trials with Allergen Specific Immunotherapy for respiratory allergy. A statement of a World Allergy Organization (WAO) taskforce," Allergy, 62(3):317-324 (2007).
Cejkova et al., "The role of conjunctival epithelial cell xanthine oxidoreductase/xanthine oxidase in oxidative reactions on the ocular surface of dry eye patients with Sjögren's syndrome," Histol Histopathol 22(9):997-1003 (Sep. 2007).
Chapple et al., "Unfolding Retinal Dystrophies: a Role for Molecular Chaperones?" Trends Mol Med, 7(9):414-421 (2001).
Chen et al., "Methazolamide Calcium Phosphate Nanoparticles in an Ocular Delivery System," Pharm Soc Japan, 130(3):419-24 (2010).
Choi et al., "Expression of Lipid Peroxidation Markers in the Tear Film and Ocular Surface of Patients with Non-Sjogren Syndrome: Potential Biomarkers for Dry Eye Disease," Curr Eye Res, 41(9):1143-11 (2016).
Ciolino et al., "Effect of alcaftadine 0.25% on ocular itch associated with seasonal or perennial allergic conjunctivitis: a pooled analysis of two multicenter randomized clinical trials," Clin Ophthalmol, 9:765-72 (May 2015).
Clinical Trials Results for Outcome Measures of Ocular Itching and Ocular Tearing (1 page) (2016).
Clinical Trials Results of Treatment with Aldehyde Trapping Compound NS2 (1 page) (2015).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
ClinicalTrials.gov identifier NCT02578914, "A Safety and Activity Study of NS2 in Subjects with Allergic Conjunctivitis," https://clinicaltrials.gov/ct2/show/NCT02578914 (6 pages) (2015).
ClinicalTrials.gov identifier NCT03162783, "A Randomized, Double Masked, Clinical Study of Subjects with Dry Eye Syndrome," (7 pages) (2017).
Cullen et al, "The small molecule aldehyde trap NS2 exhibits potent anti-inflammatory activity in three murine models of inflammation," AAAAI Annual Meeting Abstract, 1 page (Feb. 2015).
Davies, "Biopharmaceutical considerations in topical ocular drug delivery," Clin Exp Pharmacol Physiol, 27(7):558-62 (Jul. 2000).
Del Valle, "Cyclodextrins and their uses: a review," Process Biochemistry, 39(9):1033-1046 (2004).
Demir et al., "Oxidative stress of intracameral lidocaine and levobupivacaine on ocular tissues," Br J Ophthalmol, 94(8):1083-7 (Aug. 2010).
Demir et al., "The protective effect of alpha-lipoic acid against oxidative damage in rabbit conjunctiva and cornea exposed to ultraviolet radiation," Ophthalmologica, 219(1):49-53 (Jan.-Feb. 2005).
Devillier et al., "The allergen challenge chamber: A valuable tool for optimizing the clinical development of pollen immunotherapy," Allergy, 2011; 66(2):163-9.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, 33 pages. (Nov. 2014).
Esterbauer et al., "Chemistry and Biochemistry of 4-Hydroxynonenal, Malonaldehyde and Related Aldehydes," Free Radic Biol Med, 11:81-128 (1991).
European Supplementary Partial Search Report issued by the European Patent Office for European Patent Application No. 13865015.5 dated Mar. 31, 2016 (9 pages).
European Supplementary Partial Search Report issued by the European Patent Office for European Patent Application No. 14743711.5 dated Jul. 20, 2016 (14 pages).
Everest-Todd, "Topical Application of Cyclodextrin Ethers in the Control of Pain," Proceedings of the Eighth International Symposium on Cyclodextrins, pp. 495-498 (1998).
FDA, "BAM R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Gasper et al., "2-Hydroxypropyl-beta-cyclodextrin (HP?CD) reduces age-related lipofuscin accumulation through a cholesterol-associated pathway," Scientific Reports, 7(2197):1-7 (2017).
Gibson et al., "The Aldehyde Trap NS2 Mitigates Dense Haze in a Rabbit Model of Photorefractive Keratectomy" ARVO Annual Meeting Abstract, 1 page (Jun. 2015).
Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 41(3):145-55 (May 2015).
Green et al., "Influence of Various Agents on Corneal Permeability," American Journal of Ophthalmology, 72(5):897-905 (1971).
Grotto et al., "Importance of the lipid peroxidation biomarkers and methodological aspects for malondialdehyde quantification," Quim Nova, 32(1):169-174 (2009).
Herbort et al., "Endotoxin-induced uveitis in the rat," Graefe's Arch Clin Exp Ophthalmol, 226:553-8 (1988).
Hessen et al., "Dry Eye: an Inflammatory Ocular Disease," J Ophthalmic Vis Res, 9(2):240-250 (2014).
Hom et al., "Allergic conjunctivitis and dry eye syndrome," Ann Allergy Asthma Immunol, 108(3):163-6 (Mar. 2012).
International Preliminary Report on Patentability issued by the United States Patent and Trademark Office as International Searching Authority for International Application No. PCT/US2014/012762 dated Jul. 28, 2015 (8 pages).
International Search Report and Written Opinion issued by the European Patent Office as International Searching Authority for International Patent Application No. PCT/US2019/044929 dated Nov. 20, 2019 (15 pages).
International Search Report and Written Opinion issued by the United States Patent and Trademark Office as International Searching Authority for International Application No. PCT/US2010/059719 dated Feb. 8, 2011 (7 pages).
International Search Report and Written Opinion issued by the United States Patent and Trademark Office as International Searching Authority for International Application No. PCT/US2014/012762 dated Jul. 18, 2014 (11 pages).
International Search Report and Written Opinion issued by the United States Patent and Trademark Office as International Searching Authority for International Application No. PCT/US2017/047945 dated Oct. 20, 2017 (9 pages).

(56) References Cited

OTHER PUBLICATIONS

International Search Report and Written Opinion issued by the United States Patent and Trademark Office as International Searching Authority for International Patent Application No. PCT/US2017/020020 dated May 24, 2017 (12 pages).
International Search Report and Written Opinion issued by the United States Patent and Trademark Office as International Searching Authority for International Patent Application No. PCT/US2017/031808 dated Aug. 11, 2017 (10 pages).
International Search Report and Written Opinion issued by the United States Patent and Trademark Office as International Searching Authority for International Patent Application No. PCT/US2017/047958 dated Oct. 31, 2017 (10 pages).
International Search Report and Written Opinion issued by the United States Patent and Trademark Office as International Searching Authority for International Patent Application No. PCT/US2018/023000 dated Jun. 1, 2018 (8 pages).
International Search Report and Written Opinion issued by the United States Patent and Trademark Office as International Searching Authority for International Patent Application No. PCT/US2018/055310 dated Jan. 29, 2019 (9 pages).
International Search Report and Written Opinion issued by the United States Patent and Trademark Office as International Searching Authority for International Patent Application No. PCT/US2019/041942 dated Sep. 30, 2019 (18 pages).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Johannsdottir et al., "Development of a Cyclodextrin-Based Aqueous Cyclosporin A Eye Drop Formulations," International Journal of Pharmaceutics, 493(1-2):86-95 (2015).
Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, 26(3):245-248 (2010).
Kam et al., "Topical Cyclodextrin Reduces Amyloid Beta and Inflammation Improving Retinal Function in Ageing Mice," Experimental Eye Research, 135:59-66 (2015).
Knapp et al., "Intraocular Availability of Topically Applied Mycophenolate Mofetil in Rabbits," J. Ocul. Pharmacol. Ther., 19(2):181-192 (2003).
La Rosa et al., "Allergic conjunctivitis: a comprehensive review of the literature," Ital J Pediatr, 39:18 (2013).
Leonardi et al., "Correlation Between Conjunctival Provocation Test (CPT) and Systemic Allergometric Tests in Allergic Conjunctivitis," Eye, 4:760-764 (1990).
Leonardi, "Allergy and allergic mediators in tears," Exp. Eye Res., 2013; 117:106-17.
Liang et al., "Ocular safety of cationic emulsion of cyclosporine in an in vitro corneal wound-healing model and an acute in vivo rabbit model," Mol Vis, 18:2195-204 (2012).
Loftsson et al., "Cyclodextrin Microparticles for Drug Delivery to the Posterior Segment of the Eye: Aqueous Dexamethasone Eye Drops," Journal of Pharmacy and Pharmacology, 59(5):629-635 (2007).
Loftsson et al., "Cyclodextrins in Eye Drop Formulations: Enhanced Topical Delivery of Corticosteroids to the Eye," Acta Ophthalmologica Scandinavica, 80(2):144-150 (2002).
Lopachin et al., "Molecular mechanisms of aldehyde toxicity: a chemical perspective," Chem Res Toxicol, 27(7):1081-91 (Jul. 2014).
Macdonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
Macdonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).

Macdonald et al., "Novel Small Molecule Aldehyde Sequestering Agents Demonstrate Broad Therapeutic Potential for Ocular Inflammation," ARVO Annual Meeting Abstract, 2 pages (Jul. 2018).
Macdonald et al., "The novel aldehyde trap, ADX-102, reduces inflammation-mediated lung infilrate in a mouse model of LPS-induced acute lung injury," 13th World Congress on Inflammation Abstract, p. 192 (Jul. 2017).
Maeda et al., "Primary amines protect against retinal degeneration in mouse models of retinopathies," Nat Chem Biol, 8(2):170-178 (Dec. 2011).
Mandell et al., "The Aldehyde Trap NS2 Reduces Ocular Inflammation in an Endotoxin-Induced Model in Rats," ARVO Annual Meeting Abstract, 2 pages (Jun. 2015).
Maurice et al., "Advances in targeting cyclic nucleotide phosphodiesterases," Nat Rev Drug Discov., 13:290-314 (2014).
Mccord et al., "Superoxide dismutase. An enzymic function for erythrocuprein (hemocuprein).," J. Biol. Chem., 244: 6049-6055 (1969).
Mclaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 34(10):1245-1251 (2015).
Mishra et al., "Recent Patents and Emerging Therapeutics in the Treatment of Allergic Conjunctivitis," Recent Pat. Inflamm. Allergy Drug Discov.; 2011; 5(1):26-36.
Nagai et al., Improved corneal toxicity and permeability of tranilast by the preparation of ophthalmic formulations containing its nanoparticles, J Oleo Sci, 63(2):177-86 (2014).
Nakamura et al., "Involvement of Oxidative Stress on Corneal Epithelial Alterations in a Blink-Suppressed Dry Eye," Investigative Ophthalmology and Visual Science, 48(4):1552-1558 (2007).
Negre-Salvayre et al., "Advanced Lipid Peroxidation End Products in Oxidative Damage to Proteins. Potential Role in Diseases and Therapeutic Prospects for the Inhibitors," Br J Pharmacol, 153(1):6-20 (2008).
Niwa et al., "Protein oxidative damage in the stratum corneum: Evidence for a link between environmental oxidants and the changing prevalence and nature of atopic dermatitis in Japan," Br J Dermatol., 149:248 (2003).
Nociari et al., "Beta cyclodextrins bind, stabilize, and remove lipofuscin bisretinoids from retinal pigment epithelium," Proc Natl Acad Sci U.S.A E1402-E1408 (2014).
O'Brien et al., "Aldehyde Sources, Metabolism, Molecular Toxicity Mechanisms, and Possible Effects on Human Health," Crit Rev Toxicol, 35:609-662 (2005).
PCT International Search Report from PCT/US2019/054263 dated Jan. 6, 2020 (13 pages).
Pfaar et al., "Perspectives in allergen immunotherapy: 2017 and beyond," Allergy, 2018; 73(Suppl 104):5-23.
Pontikis et al., "Cyclodextrin alleviates neuronal storage of cholesterol in Niemann-Pick C disease without evidence of detectable blood-brain barrier permeability," Journal of Inherited Metabolic Disease, 36(3):491-498 (2013).
Pred Forte Prescribing Information, Allergan, 5 pages (2017).
Pubchem, SCHEMBL16316728, CID 117758222, Feb. 23, 2016 (13 pages).
Rajewski et al., "Pharmaceutical applications of cyclodextrins. 2. In vivo drug delivery," J Pharm Sci, 85(11):1142-69 (Nov. 1996).
Rauli et al., "Validation of Malondialdehyde and 4-Hydroxy-2-trans-Nonenal Measurement in Plasma by NICI-GC-MS1," J Biochem, 123:918-923 (1998).
Restasis® Prescribing Information, Allergan, copyright 2016, revised 2017 (15 pages).
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo et al., "Endogenous antioxidants and radical scavengers," Advances in Experimental Medicine and Biology, 698:52-6 (2010).

(56) References Cited

OTHER PUBLICATIONS

Rizzo, Fatty aldehyde and fatty alcohol metabolism: review and importance for epidermal structure and function, Biochim Biophys Acta, 1841(3):377-89 (Mar. 2014).
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Scleritis," Merck Manual Professional Version, 3 pages (2016), Available at: https://www.merckmanuals.com/professional/eye-disorders/conjunctival-and-scleral-disorders/scleritis.
Rønborg et al., "Exposure chamber for allergen challenge. The development and validation of a new concept," Allergy, 1996; 51(2):82-8.
Sanchez et al., "Allergic Conjunctivitis," J Investig Allergol Clin Immunol, 21(2):1-19 (2011).
Sandikci et al., "Lipid Peroxidation and Antioxidant Defence System in Patients with Active or Inactive Behcet's Disease," Acta Derm Venereol, 83:342-346 (2003).
Sasaki et al., "Retinal drug delivery using eyedrop preparations of poly-L-lysine-modified liposomes," Eur J Pharm Biopharm, 83(3):364-9 (2013).
Satici et al., "Malondialdehyde and antioxidant enzyme levels in the aqueous humor of rabbits in endotoxin-induced uveitis," Eur J Ophthalmol, 13(9-10):779-83 (Nov.-Dec. 2003).
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 127(6):763-768 (Jun. 2009).
Schaumberg et al., "Prevalence of Dry Eye Syndrome Among US Women," Am J Ophthalmol, 136(2):318-326 (Aug. 2003).
Search Report and Written Opinion issued by the Intellectual Property Office of Singapore for Singapore Patent Application No. 11201504859Y dated Aug. 1, 2016 (12 pages).
Sheppard et al., Targeting Anterior Uveitis: A Focus on Iontophoresis and Other Advanced Technologies, Sep. 1, 2018 [Retrieved Nov. 11, 2019] Retrieved from Internet URL: https://www.nyee.edu/files/NYEE/Health%20Professionals/Continuing%20Medical%20Education/Enduring%20CME%20Activities/158_supplernent.smaU_v 1_FINAL %20082818.pdf (8 pages).
Singh et al., "The epidemiology of ocular and nasal allergy in the United States, 1988-1994," J. Allergy Clin. Immunol., 2010; 126(4):778-783.
Smith et al., "Basic pathogenic mechanisms operating in experimental models of acute anterior uveitis," Immunol Cell Biol, 76:497-512 (1998).
Stevenson et al., "Dry eye disease: an immune-mediated ocular surface disorder," Arch Ophthalmol. 2012; 130(1): 90-100.
Study showing effect of ADX-102 on Fibrotic Changes in Cardiac Fibroblasts Following Cell Stress, American Society for Cell Biology Annual Meeting, Dec. 3-7, 2016 (2 pages).
Tang-Liu et al., "Effects of four penetration enhancers on corneal permeability of drugs in vitro," Journal of Pharmaceutical Sciences, 83(1):85-90 (1994).
Tempest-Roe et al., "Local therapies for inflammatory eye disease in translation: past, present and future," BMC Ophthalmol, 13(1):39 (Aug. 2013).
Tukozkan et al., "Measurement of Total Malondialdehyde in Plasma and tissues by High-Performance Liquid Chromatography and Thiobarbituric Acid Assay," Firat Tip Dergisi, 11(2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wakamatsu et al., "Evaluation of lipid oxidative stress status and inflammation in atopic ocular surface disease," Mol Vis, 16:2465-75 (Nov. 2010).
Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).
Yadav et al., "Regulation of NF-κB-Induced Inflammatory Signaling by Lipid Peroxidation-Derived Aldehydes," Oxidative Med & Cell Longev, 2013, Art ID 690545, 11 pages (2013).
Zarkovic "4-hydroxynonenal and neurodegenerative diseases," Molecular Aspects of Medicine, 24(4-5):293-303 (2003).
Zhou et al., "Mechanisms for the induction of HNE- MDA- and AGE-adducts, RAGE and VEGF in retinal pigment epithelial cells," Exp Eye Res., 80(4):567-80 (2005).
"Malondialdehyde," WikipediA, retrieved from Internet URL: "https://en.wikipedia.org/w/index.php?title=Malondialdehyde&oldid=993228459" on Aug. 4, 2021. Page last edited Dec. 9, 2020. (4 pages).
Aldeyra Press Release—Aldeyra Therapeutics Announces Positive Results from Dry Eye Disease Phase 2a Clinical Trial, Sep. 12, 2017 (3 pages).
Aldeyra Press Release—Aldeyra Therapeutics Announces Positive Top-Line Symptom and Sign Results from Run-In Cohort of Phase 3 Tranquility Trial in Dry Eye Disease, Jan. 7, 2021 (3 pages).
Aldeyra Press Release—Aldeyra Therapeutics Presents Dry Eye Disease Phase 2a Clinical Trial Results at the Association for Research in Vision and Ophthalmology 2018 Annual Meeting, May 1, 2018 (2 pages).
Clinical Trials Results of Treatment with NS2 Topical Formulation (1 page) (2015).
Gibson et al., "The Aldehyde Trap NS2 Mitigates Dense Haze in a Rabbit Model of Photorefractive Keratectomy" Poster presented at ARVO Annual Meeting, 1 page (May 3-7, 2015).
Gole et al., "Plasma proteins modified by tyrosine nitration in acute respiratory distress syndrome," Am J Physiol Lung Cell Mol Physiol. 2000; 278(5):L961-7.
International Search Report and Written Opinion from PCT/US2022/011604 dated Mar. 4, 2022.
International Search Report and Written Opinion issued by the United States Patent and Trademark Office as International Searching Authority for International Patent Application No. PCT/US2019/052961, dated Dec. 10, 2019 (11 pages).
International Search Report and Written Opinion issued by the United States Patent and Trademark Office as International Searching Authority for International Patent Application No. PCT/US2019/064669, dated Feb. 27, 2020 (12 pages).
International Search Report and Written Opinion issued by the United States Patent and Trademark Office as International Searching Authority for International Patent Application No. PCT/US2020/024022, dated Jun. 17, 2020 (11 pages).
International Search Report and Written Opinion issued by the United States Patent and Trademark Office as International Searching Authority for International Patent Application No. PCT/US2020/031138, dated Jul. 13, 2020 (7 pages).
International Search Report and Written Opinion issued by the United States Patent and Trademark Office as International Searching Authority for International Patent Application No. PCT/US2020/031219, dated Aug. 31, 2020 (14 pages).
International Search Report and Written Opinion issued by the United States Patent and Trademark Office as International Searching Authority for International Patent Application No. PCT/US2021/023884, dated Jul. 28, 2021 (11 pages).
International Search Report and Written Opinion issued by the United States Patent and Trademark Office as International Searching Authority for International Patent Application No. PCT/US2021/027148, dated Jun. 28, 2021 (9 pages).
International Search Report and Written Opinion issued by the United States Patent and Trademark Office as International Search-

(56) References Cited

OTHER PUBLICATIONS ing Authority for International Patent Application No. PCT/US2021/032335, dated Jul. 27, 2021 (11 pages).
International Search Report and Written Opinion issued by the United States Patent and Trademark Office as International Searching Authority for International Patent Application No. PCT/US2021/035948, dated Oct. 26, 2021 (12 pages).
Keister et al., "Inflammatory Bowel Disease and Irritable Bowel Syndrome Similarities and Differences," Crohn's & Colitis Foundation of America. 2014; 12 pages.
Ousler et al., "Use of the Controlled Adverse Environment (CAE) in Clinical Research: A Review," Ophthalmol Ther. 2017;6(2):263-276.
Pubchem, 1824609-67-7, SID 333824451, Apr. 24, 2017 (6 pages).
Pubchem, 2-(3-Aminoquinolin-2-yl)propan-2-ol, CID 117758222, Feb. 23, 2016, modified Jun. 13, 2020 (11 pages).
Roumen et al. "Serum lipofuscin as a prognostic indicator of adult respiratory distress syndrome and multiple organ failure," Br J Surg. 1994; 81(9):1300-5.
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017; 58(8):1231.
Stefansson, et al., "Cyclodextrins in Eye Drop Formulations," Journal of Inclusion Phenomena. 2002; 44:23-27; Abstract only, printed from https://insights.ovid.com/jinpmr/200244010/00984572-200244010-00006#, 2 pages.

\* cited by examiner

ID 690545), molecular dysfunction (O'Brien et al., Critical Reviews in Toxicology, 2005, 35(7):609-62), and the accumulation of indigestible metabolites, such as lipofuscin components in the retina (Boyer et al., J Biol Chem., 2012, 287:22276-86).

In biological systems, aldehydes are formed by a variety of processes, including the oxidation of alcohols, polyamine and glucose metabolism, and oxidative stress. In some disease states, aldehyde concentrations may be increased. Increases in aldehyde concentrations, particularly malonyldialdehyde (MDA), which is thought to be most commonly derived from lipid peroxidation, has been described in a variety of inflammatory ocular diseases, including pterygium, Behcet's Disease, Sjögren's Syndrome, anterior uveitis, and dry eye disease (Sandikci et al., Acta Dermato-Venereologica, 2003, 83(5):342-6; Cejkova et al., Histology and Histopathology, 2007, 22(9):997-1003; Balci et al., Molecular Vision, 2011, 17:443-7; Turk et al., Ocular Immunology and Inflammation, 2014, 22(2):127-32; Choi et al., Current Eye Research, 2016, 41(9):1143-9).

Thus, there is an unmet need for improved ophthalmic formulations of drugs capable of treating allergic conjunctivitis.

OPHTHALMIC FORMULATIONS AND USES THEREOF

CROSS-REFERENCE TO RELATED APPLICATIONS

This application claims the benefit under 35 U.S.C. § 119(e) of U.S. provisional application No. 62/824,233, filed Mar. 26, 2019, and U.S. provisional application No. 62/857,874, filed Jun. 6, 2019, the contents of each of which is incorporated by reference herein in their entireties.

TECHNICAL FIELD

The present invention relates to ophthalmic solutions comprising reproxalap, or a pharmaceutically acceptable salt thereof, for treatment of a disease or disorder such as allergic conjunctivitis (AC).

BACKGROUND

Acute allergic conjunctivitis (AC) is experienced by approximately 40% of the general population (Singh et al., J Allergy Clin Immunol., 2010, 126(4):778-783). AC is associated with Type I (immediate) hypersensitivity reactions, which involve immunoglobulin E (IgE)-mediated release of histamine and other mediators from mast cells and basophils. Mast cell degranulation leads to release of inflammatory mediators and activation of enzymatic cascades generating pro-inflammatory mediators (Mishra et al., Recent Pat Inflamm Allergy Drug Discov., 2011, 5(1):26-36). In the eye, release of a variety of mediators leads to inflammation of the conjunctival mucosa that also affects the cornea and eyelids, resulting in symptoms that include itching and burning, tearing, chemosis (conjunctival edema), conjunctival injection, hyperemia, eyelid edema, and mucus discharge.

The early symptoms of allergic conjunctivitis, occurring within minutes of allergen exposure, are likely due primarily to the release of histamine (Leonardi, A., Exp Eye Res. 2013, 117:106-17), which peaks in tears about five minutes after exposure to allergen and significantly diminishes over 30 to 40 minutes (Ackerman et al., Ther Adv Chronic Dis., 2016, 7(1):52-67.2016) Immediately following the rapid rise and fall of histamine, the symptoms of allergic conjunctivitis are perpetuated by non-histaminic inflammatory mediators, such as cellular infiltrate, cytokines, leukotrienes, proteases, and other factors (Leonardi, A., Exp Eye Res., 2013, 117: 106-17), including aldehydes. Aldehydes are pro-inflammatory mediators of both allergic (Th2) and autoimmune (Th1) diseases, and elevated levels of toxic aldehydes are associated with allergic conjunctivitis and other ocular and systemic diseases (Bacsi et al., J Allergy Clin Immunol., 2005, 116(4): 836-843; Boldogh et al., J Clin Invest., 2005, 115(8): 2169-2179; Wakamatsu et al., Mol Vis., 2010, 16: 2465-2475).

Aldehydes are reactive and bind to proteins, carbohydrates, lipids and nucleic acids (Esterbauer et al., Free Radical Biology and Medicine, 1990, 11(1):81-128). Free aldehydes—aldehydes not sequestered or otherwise protected in specific metabolic processes—can be toxic, and aldehyde binding to cellular constituents can lead to inflammation (Yadav et al., Oxidative Medicine and Cellular Longevity 2013, Volume 2013, Article

SUMMARY

In one aspect, the present invention relates to an ophthalmic solution comprising reproxalap, or a pharmaceutically acceptable salt thereof, and a pharmaceutically acceptable excipient, wherein the concentration of reproxalap, or a pharmaceutically acceptable salt thereof, is about 0.5% w/v or less and about 0.1% w/v or greater. In some embodiments, the reproxalap and a cyclodextrin excipient in the ophthalmic solution in a less than 1:2.1 molar ratio. In some embodiments, concentration of reproxalap, or a pharmaceutically acceptable salt thereof, is about 0.2% w/v to about 0.3% w/v.

In some embodiments, the ophthalmic solution comprises about 0.25% w/v reproxalap and a pharmaceutically acceptable excipient selected from a cyclodextrin. In some embodiments, the cyclodextrin is at about 7% w/v. In some embodiments, the cyclodextrin is at about 11% w/v. In some embodiments, the cyclodextrin is sulfobutylether-β-cyclodextrin or hydroxypropyl-β-cyclodextrin.

In some embodiments, the ophthalmic solution comprises about 0.5% w/v reproxalap and a pharmaceutically acceptable excipient selected from a cyclodextrin. In some embodiments, the cyclodextrin is at about 9.5% w/v. In some embodiments, the cyclodextrin is sulfobutylether-β-cyclodextrin or hydroxypropyl-β-cyclodextrin.

In another aspect, the present invention relates to a method for treating allergic conjunctivitis in a subject, comprising topically administering to any eye of a subject in need thereof a therapeutically effective amount of an ophthalmic solution of the invention. In some embodiments, the allergic conjunctivitis treated is seasonal allergic conjunctivitis. In some embodiments, the allergic conjunctivitis treated is contact conjunctivitis. In some embodiments, the allergic conjunctivitis treated is perennial conjunctivitis.

In some embodiments of the method, an ophthalmic solution of the invention is administered prior to exposure of the subject to an eye allergen. In some embodiments, the ophthalmic solution is administered to an eye of a subject in need thereof in the time period for durability of the therapeutic effect, e.g., for a 0.25% w/v or 0.5% w/v reproxalap solution, prior to an expected or certain exposure to an eye allergen. In some embodiments, the ophthalmic solution is administered 3.5 h or less, 3 h or less, 2.5 h or less, 2 h or less, 1.5 h or less, 1 h or less, 0.5 h or less, 25 min or less, 20 min or less, 25 min or less, 20 min or less, 15 min or less, 10 min or less, or 5 min or less before an expected or certain exposure to an eye allergen, or immediately prior to an expected or certain exposure to an eye allergen.

In some embodiments, the subject for treatment prior to an expected or certain exposure to an eye allergen has a history of allergic conjunctivitis. In some embodiments, the subject for treatment prior to an expected or certain exposure to an eye allergen has a history of allergic conjunctivitis and has a positive allergen skin test for one or more eye allergens. In some embodiments, the subject for treatment prior to an expected or certain exposure to an eye allergen has been previously clinically diagnosed with allergic conjunctivitis. In some embodiments, the subject for treatment prior to an expected or certain exposure to an eye allergen has been previously clinically diagnosed with allergic conjunctivitis, and has a positive allergen skin test for one or more eye allergens.

In some embodiments of the method, an ophthalmic solution of the invention is administered at or after exposure to an eye allergen. In some embodiments, the ophthalmic solution of the invention is administered immediately after exposure to an eye allergen. In some embodiments, the ophthalmic solution of the invention is administered at or after the onset of symptoms of allergic conjunctivitis. In some embodiments, a method for treating allergic conjunctivitis in a subject comprises topically administering to an eye of a subject in need thereof an ophthalmic solution of the invention at or after exposure to an eye allergen, or at or after onset of symptoms of allergic conjunctivitis, where the ophthalmic solution is administered six times a day, five times a day, four times a day (QID), three times a day (TID), two times a day (BID), once a day (QD), or as needed (PRN). In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where the ophthalmic solution is administered six times a day, five times a day, four times a day (QID), three times a day (TID), two times a day (BID), once a day (QD), followed by administration as needed (PRN). In some embodiments of the method, an ophthalmic solution of the invention is administered four times a day (QID) followed by administration as needed (PRN).

In some embodiments, the treatment at or after exposure to an eye allergen or at or after the onset of symptoms of allergic conjunctivitis can be further divided into treatment in an initiation phase, exacerbation phase, and/or maintenance phase. In some embodiments, the ophthalmic solution is administered six times a day, five times a day, or four times a day (QID) in the initiation phase and/or exacerbation phase, followed by two times a day (BID), once a day (QD) or as needed (PRN) in the maintenance phase.

In some embodiments, a method for treating allergic conjunctivitis comprises administering to an eye of a subject in need thereof an ophthalmic solution of the invention prior to an expected or certain exposure to an eye allergen; and further comprising administering an ophthalmic solution of the invention to the eye of the subject at or after exposure to the eye allergen, or at or after onset of symptoms of allergic conjunctivitis. In some embodiments, a method of treating allergic conjunctivitis comprises a first treatment phase and a second treatment phase, wherein the first treatment phase comprises administering an ophthalmic solution of the invention to an eye of a subject in need thereof prior to an expected or certain exposure to an eye allergen, or immediately prior to expected or certain exposure to an eye allergen, and the second treatment phrase comprises administering an ophthalmic solution of the invention to the eye at or after exposure to an eye allergen, or at or after the onset of symptoms of allergic conjunctivitis.

In some embodiments, in the first treatment phase of this two phase treatment regimen, an ophthalmic solution of the invention is administered 3.5 h or less, 3 h or less, 2.5 h or less, 2 h or less, 1.5 h or less, 1 h or less, 0.5 h or less, 25 min or less, 20 min or less, 25 min or less, 20 min or less, 15 min or less, 10 min or less, or 5 min or less prior to an expected or certain exposure to an eye allergen, or immediately prior to expected or certain exposure to an eye allergen.

In some embodiments, in the second treatment phase, an ophthalmic solution of the invention is administered within 5 min, 10 min, 15 min, 20 min, 25 min, 30 min, 35 min, 40 min, 45 min, 50 min, 60 min (1 h), 75 min (1.25 h), 90 min (1.5 h), 105 min (1.75 h), or 120 min (2 h) of exposure to an eye allergen or after the onset of symptoms of allergic conjunctivitis. In some embodiments, in the second treatment phase, an ophthalmic solution of the invention is administered six times a day, five times a day, four times a day (QID), three times a day (TID), two times a day (BID), once a day (QD) or as needed (PRN). In some embodiments, in the second treatment phase, an ophthalmic solution of the invention is administered six times a day, five times a day, four times a day (QID), three times a day (TID), two times a day (BID), once a day (QD), followed by administration as needed (PRN). In some embodiments, in the second treatment phase, an ophthalmic solution of the invention is administered four times a day (QID) followed by administration as needed (PRN).

In some embodiments, the second treatment phase can be further divided into treatment in an initiation phase, exacerbation phase, and/or maintenance phase. In some embodiments, the ophthalmic solution is administered six times a day, five times a day, or four times a day (QID) in the initiation phase and/or exacerbation phase, followed by two times a day (BID), once a day (QD) or as needed (PRN) in the maintenance phase.

DETAILED DESCRIPTION

1. General Description of Certain Embodiments

Figure 1:
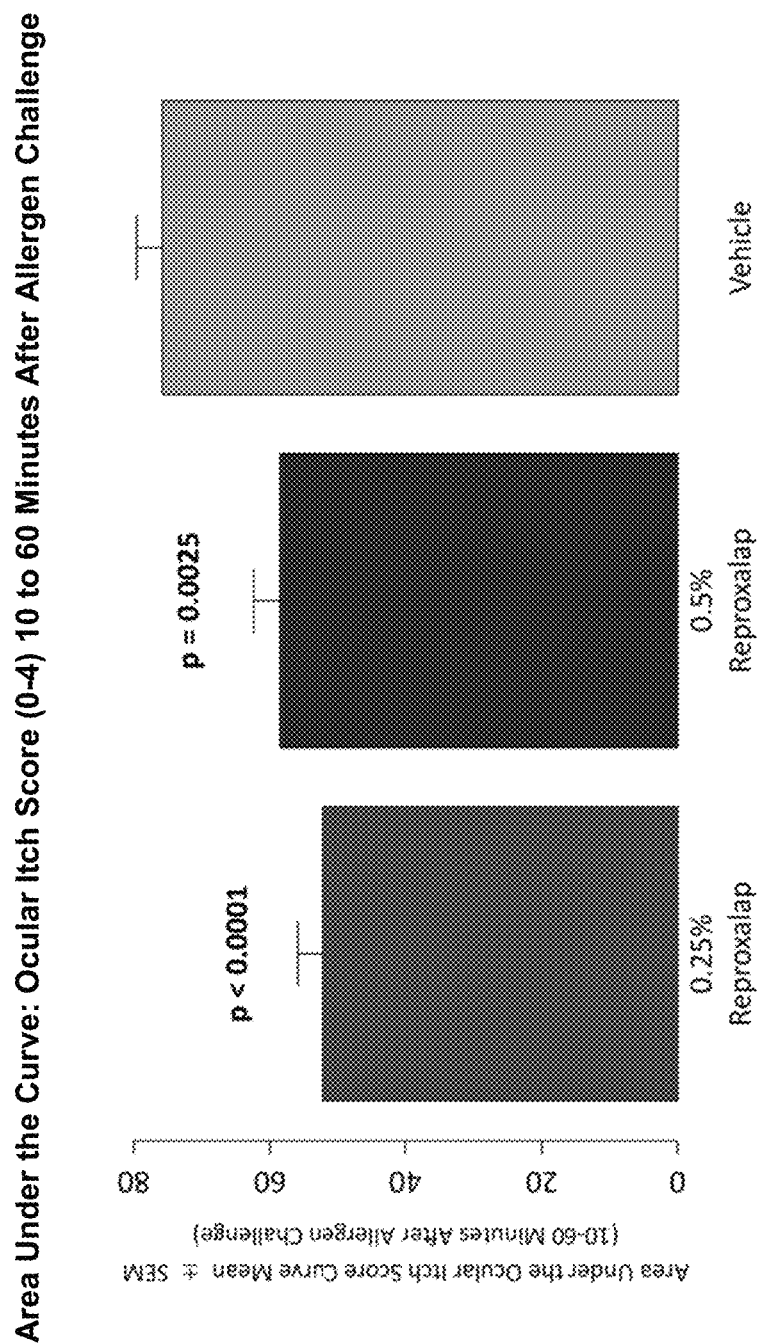
FIG. 1 depicts area under the curve calculations (AUC) for Ocular Itch Score (0-4) 10 to 60 minutes after allergen challenge. SEM=Standard error of the mean; Ocular Itch Scale 0 (no itch) to 4 (incapacitating itch).

Reproxalap topical ocular solution is being developed for treatment of ocular inflammation. The drug product, in various strengths, has completed a Phase 1 clinical trial, as well as a controlled, double-masked Phase 2a clinical trial in allergic conjunctivitis, a controlled, double-masked Phase 2b clinical trial in allergic conjunctivitis, a controlled, double-masked Phase 2 clinical trial in noninfectious anterior uveitis, a Phase 2a clinical trial in dry eye disease, and a controlled, double-masked Phase 2b clinical trial in dry eye disease. The maximum exposure to reproxalap in these completed clinical trials has been dosing with 0.5% w/v strength for six weeks, for treating subjects with noninfectious anterior uveitis.

It has now been found that certain topical (ophthalmic) formulations (e.g., solutions) of reproxalap are surprisingly effective in treating allergic conjunctivitis. Without wishing to be bound by theory, it is believed that certain concentrations of reproxalap in combination with excipients and/or ratios of reproxalap to excipients exhibit increased efficacy over previous ophthalmic solutions of reproxalap. Furthermore, in some embodiments, the presently disclosed topical formulations result in reduced instillation site pain and irritation in human patients relative to previously known ophthalmic solutions of reproxalap. In some embodiments, reduced instillation site pain and irritation leads to increased patient compliance and improved outcomes.

In some embodiments, the presently disclosed ophthalmic solutions exhibit an improved (e.g., extended) release of reproxalap in comparison with previously known reproxalap ophthalmic solutions. Without wishing to be bound by theory, it is believed that the presently disclosed ophthalmic solutions may provide extended or delayed release of reproxalap due to interactions of reproxalap with the excipient(s). In some embodiments, particular ratios of reproxalap: excipient(s) in the presently disclosed ophthalmic solutions exhibit increased efficacy.

In some embodiments, after administration to a patient population, an ophthalmic solution of the present disclosure provides a statistically significant reduction in the ocular itch scale of a patient population suffering from allergic conjunctivitis. In some embodiments, after administration to a patient population, an ophthalmic solution of the present disclosure provides a statistically significant ($p<0.05$) reduction by at least 1 point in the ocular itch scale of a patient population suffering from allergic conjunctivitis. In some embodiments, after administration to a patient population, an ophthalmic solution of the present disclosure provides a statistically significant ($p<0.05$) reduction by at least 2 points in the ocular itch scale of a patient population suffering from allergic conjunctivitis. Ocular Itch Scale 0 (no itch) to 4 (incapacitating itch).

In some embodiments, the present invention provides an ophthalmic solution comprising reproxalap, or a pharmaceutically acceptable salt thereof, and a pharmaceutically acceptable excipient, wherein the concentration of reproxalap, or a pharmaceutically acceptable salt thereof, is about 0.5% w/v or less and 0.1% w/v or greater. In some embodiments, the present invention provides a method for treating allergic conjunctivitis in a subject, comprising topically administering an ophthalmic solution described herein to the subject in need thereof.

In some embodiments, a disclosed ophthalmic solution comprises reproxalap and a cyclodextrin excipient in a less than 1:2.1 molar ratio. In some embodiments, the ratio is a 1:2.1 to about 1:25 ratio. In some embodiments, the ratio is about 1:2.2 to 1:20, 1:2.5 to 1:20, 1:2.5 to 1:10, 1:2.75 to 1:10, 1:3 to 1:8, 1:3.5 to 1:7, 1:4 to 1:6, or 1:4 to 1:5. In some embodiments, the ratio is about 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4.0, 1:4.1, 1:4.2, 1:4.3, 1:4.4, 1:4.5, 1:4.6, 1:4.7, 1:4.8, 1:4.9, 1:5.0, 1:5.1, 1:5.2, 1:5.3, 1:5.4, 1:5.5, 1:6, 1:7, 1:8, 1:9, 1:10, 1:12, 1:15, 1:20, or 1:25. In some embodiments, the ratio is one of those in Table 1, below, e.g. a ratio in Table 1+/−10%. In some embodiments, the cyclodextrin is sulfobutylether β-cyclodextrin (SBECD). In some embodiments, the cyclodextrin is hydroxypropyl-β-cyclodextrin (2-hydroxypropyl-β-cyclodextrin: HPCD).

In some embodiments, the cyclodextrin excipient is one of those described herein, such as sulfobutylether β-cyclodextrin (SBECD).

TABLE 1

Reproxalap Ophthalmic Solutions

| Formulation (reproxalap/ SBECD, % w/v) | reproxalap (g/L) | SBECD (g/L) | SBECD * (MW = 2163 g/mole) | reproxalap (MW = 236.7 g/mole) | Molar ratio (SBECD/ Reproxalap) | |
|---|---|---|---|---|---|---|
| 0.25/7 | 2.5 | 70 | 0.032 | 0.011 | 3.06 | ~3 moles of SBECD per mole of API |
| 0.5/9.5 | 5 | 95 | 0.044 | 0.021 | 2.08 | ~2 moles of SBECD per mole of API |
| 0.25/11 | 2.5 | 110 | 0.051 | 0.011 | 4.81 | ~5 moles of SBECD per mole of API |

* average degree of substitution = 6.5.

In some embodiments, the ophthalmic solution comprises about 0.2% to 0.4% reproxalap and about 7% to 25% w/v of a cyclodextrin excipient, such as SBECD or HPCD. In some embodiments, the ophthalmic solution comprises about 0.2%, 0.25%, 0.3%, 0.35%, or 0.4% reproxalap and about 7% to 25% w/v of a cyclodextrin excipient, such as SBECD or HPCD.

In some embodiments, the ophthalmic solution comprises about 0.25% reproxalap and about 4.7% to about 25% w/v of a cyclodextrin excipient such as SBECD or HPCD.

In some embodiments, the ophthalmic solution comprises about 0.25% reproxalap and about 7% to 25% w/v of a cyclodextrin excipient such as SBECD or HPCD.

In some embodiments, the ophthalmic solution comprises about 0.25% reproxalap and about 4.75% to about 11% w/v of a cyclodextrin excipient such as SBECD or HPCD.

In some embodiments, the ophthalmic solution comprises about 0.5% reproxalap and about 9.5% to about 11% w/v of a cyclodextrin excipient such as SBECD or HPCD.

In some embodiments, the ophthalmic solution comprises about 0.25% reproxalap and about 7% w/v of a cyclodextrin excipient such as SBECD or HPCD.

In some embodiments, the ophthalmic solution comprises about 0.25% reproxalap and about 11% w/v of a cyclodextrin excipient such as SBECD or HPCD.

2. Definitions

The general terms used herein are defined with the following meanings, unless explicitly stated otherwise.

The term "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "pharmaceutically acceptable" is defined herein to refer to those compounds, biologic agents, materials, compositions and/or dosage forms, which are, within the scope of sound medical judgment, suitable for contact with the tissues a subject e.g., a mammal or human, without excessive toxicity, irritation allergic response and other problem complications commensurate with a reasonable benefit/risk ratio.

The term "treating" or "treatment" as used herein comprises a treatment relieving, reducing or alleviating at least one symptom in a subject or affecting a delay of progression of a disease, condition and/or disorder. For example, treatment can be the diminishment of one or several signs or symptoms of a disorder or complete eradication of a disorder. Within the meaning of the present invention, the term "treat" also denotes to arrest, delay the onset of (e.g., the period prior to clinical manifestation of a disease) and/or reduce the risk of developing or worsening a disease.

The term "subject" or "patient" as used herein includes animals, such as mammals, e.g., humans, dogs, cows, horses, pigs, sheep, goats, cats, mice, rabbits, rats and transgenic non-human animals. In some embodiments, the subject is a human.

The term "about" or "approximately" shall have the meaning of within 10% of a given value or range. In some embodiments, the term "about" refers to within 10%, 9%, 8%, 7%, 6%, 5%, 4%, 3%, 2%, or 1% of a given value.

The term "w/v" as used herein refers to "gram/mL" (weight over volume), which is a concentration unit. For example, 7% w/v is equivalent to 70 mg/mL.

Reproxalap has the following structure:

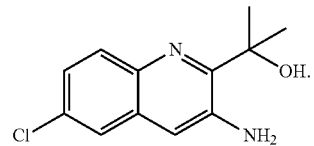 [SMILES: CC(C)(O)c1nc2ccc(Cl)cc2cc1N]

Without wishing to be bound by any particular theory, reproxalap functions as an aldehyde sequestering agent, or "trap," which binds rapidly to aldehydes and forms a cyclic product.

3. Ophthalmic Solutions

An ophthalmic solution of the invention comprises reproxalap, or a pharmaceutically acceptable salt thereof, at a concentration suitable for effectively treating allergic conjunctivitis, in particular without causing severe or intolerable adverse effects. In some embodiments, the present invention provides an ophthalmic solution comprising about 0.1% to about 0.5% w/v reproxalap, or a pharmaceutically acceptable salt thereof, and a pharmaceutically acceptable excipient, wherein the molar ratio of reproxalap to the excipient is about 1:2.1 or less.

In some embodiments, the excipient is a cyclodextrin and the ratio of reproxalap to the excipient is about 1:2.1 to about 1:25.

In some embodiments, the present invention provides an ophthalmic solution comprising reproxalap, or a pharmaceutically acceptable salt thereof, and a pharmaceutically acceptable excipient, wherein the concentration of reproxalap, or a pharmaceutically acceptable salt thereof, is about 0.5% w/v or less and about 0.1% w/v or greater. In some embodiments, the ophthalmic solution comprises 0.15 to 0.45% w/v reproxalap, or a pharmaceutically acceptable salt thereof, and a pharmaceutically acceptable excipient. In some embodiments, the ophthalmic solution comprises about 0.2 to about 0.4% w/v reproxalap, or a pharmaceutically acceptable salt thereof, and a pharmaceutically acceptable excipient. In some embodiments, the ophthalmic solution comprises about 0.21 to about 0.35% w/v reproxalap, or a pharmaceutically acceptable salt thereof, and a pharmaceutically acceptable excipient. In some embodiments, the ophthalmic solution comprises about 0.22 to about 0.3% w/v reproxalap, or a pharmaceutically acceptable salt thereof, and a pharmaceutically acceptable excipient. In some embodiments, the ophthalmic solution comprises about 0.22 to about 0.29% w/v reproxalap, or a pharmaceutically acceptable salt thereof, and a pharmaceutically acceptable excipient. In some embodiments, the ophthalmic solution comprises about 0.25% w/v reproxalap, or a pharmaceutically acceptable salt thereof, and a pharmaceutically acceptable excipient. In some embodiments, the ophthalmic solution comprises about 0.25% w/v reproxalap and a pharmaceutically acceptable excipient selected from a cyclodextrin. In some embodiments, the ophthalmic solution comprises about 0.5% w/v reproxalap and a pharmaceutically acceptable excipient selected from a cyclodextrin.

In some embodiments, the present invention provides an ophthalmic solution comprising less than 0.5% w/v reproxalap, or a pharmaceutically acceptable salt thereof, and a pharmaceutically acceptable excipient. In some embodiments, the present invention provides an ophthalmic solution comprising at least 0.1% w/v reproxalap, or a pharmaceutically acceptable salt thereof, and a pharmaceutically acceptable excipient. In some embodiments, the present invention provides an ophthalmic solution comprising reproxalap, or a pharmaceutically acceptable salt thereof, and a pharmaceutically acceptable excipient, wherein the concentration of reproxalap, or a pharmaceutically acceptable salt thereof, is less than 0.5% w/v and 0.1% w/v or greater.

In some embodiments, reproxalap, or a pharmaceutically acceptable salt thereof, in an ophthalmic solution of the invention is at a concentration of less than 0.45% w/v and at least 0.1% w/v. In some embodiments, reproxalap, or a pharmaceutically acceptable salt thereof, in an ophthalmic solution of the invention is at a concentration of less than 0.4% w/v and at least 0.1% w/v. In some embodiments, reproxalap, or a pharmaceutically acceptable salt thereof, in an ophthalmic solution of the invention is at a concentration of less than 0.35% w/v and at least 0.1% w/v. In some embodiments, reproxalap, or a pharmaceutically acceptable salt thereof, in an ophthalmic solution of the invention is at a concentration of less than 0.3% w/v and at least 0.1% w/v. In some embodiments, reproxalap, or a pharmaceutically acceptable salt thereof, in an ophthalmic solution of the invention is at a concentration of less than 0.25% w/v and more than 0.1% w/v. In some embodiments, reproxalap, or a pharmaceutically acceptable salt thereof, in an ophthalmic solution of the invention is at a concentration of less than 0.2% w/v and at least 0.1% w/v. In some embodiments, reproxalap, or a pharmaceutically acceptable salt thereof, in an ophthalmic solution of the invention is at a concentration of less than 0.15% w/v and at least 0.1% w/v.

In some embodiments, reproxalap, or a pharmaceutically acceptable salt thereof, in an ophthalmic solution of the invention is at a concentration of 0.5% w/v or less and at least 0.15% w/v. In some embodiments, reproxalap, or a pharmaceutically acceptable salt thereof, in an ophthalmic solution of the invention is at a concentration of 0.5% w/v or less and at least 0.2% w/v. In some embodiments, reproxalap, or a pharmaceutically acceptable salt thereof, in an ophthalmic solution of the invention is at a concentration of 0.5% w/v or less and at least 0.25% w/v. In some embodiments, reproxalap, or a pharmaceutically acceptable salt thereof, in an ophthalmic solution of the invention is at a concentration of 0.5% w/v or less and at least 0.3% w/v. In some embodiments, reproxalap, or a pharmaceutically acceptable salt thereof, in an ophthalmic solution of the invention is at a concentration of 0.5% w/v or less and at least 0.35% w/v. In some embodiments, reproxalap, or a pharmaceutically acceptable salt thereof, in an ophthalmic solution of the invention is at a concentration of 0.5% w/v or less and at least 0.4% w/v. In some embodiments, reproxalap, or a pharmaceutically acceptable salt thereof, in an ophthalmic solution of the invention is at a concentration of 0.5% w/v or less and at least 0.45% w/v.

In some embodiments, reproxalap, or a pharmaceutically acceptable salt thereof, in an ophthalmic solution of the invention is at a concentration of about 0.1% to 0.5%, 0.15% to 0.45% w/v, 0.15% to 0.4% w/v, 0.15% to 0.35% w/v, 0.15% to 0.3% w/v, 0.15% to 0.25% w/v, or 0.15% to 0.2% w/v. In some embodiments, reproxalap, or a pharmaceutically acceptable salt thereof, in an ophthalmic solution of the invention is at a concentration of 0.2% to 0.45% w/v, 0.2% to 0.4% w/v, 0.2% to 0.35% w/v, 0.2% to 0.3% w/v, or 0.2% to 0.25% w/v. In some embodiments, reproxalap, or a pharmaceutically acceptable salt thereof, in an ophthalmic solution of the invention is at a concentration of 0.25% to 0.45% w/v, 0.25% to 0.4% w/v, 0.25% to 0.35% w/v, or 0.25% to 0.3% w/v. In some embodiments, reproxalap, or a pharmaceutically acceptable salt thereof, in an ophthalmic solution of the invention is at a concentration of 0.3% to 0.45% w/v or 0.3% to 0.4% w/v.

In some embodiments, reproxalap, or a pharmaceutically acceptable salt thereof, in an ophthalmic solution of the invention is at a concentration of about 0.1% w/v, 0.15% w/v, about 0.2% w/v, about 0.25%, about 0.3% w/v, about 0.35% w/v, about 0.4% w/v, about 0.45% w/v, or about 0.5% w/v.

In some embodiments, as further described herein, the foregoing concentrations of reproxalap can be selected and applied to treatment regimen that includes an initiation phase, an exacerbation phase, and/or a maintenance phase, as further described herein.

In some embodiments, a pharmaceutically acceptable excipient in an ophthalmic solution of the invention is a cyclodextrin. In some embodiments, a cyclodextrin is α-, β-, or γ-cyclodextrin. In some embodiments, a cyclodextrin is a pharmaceutically acceptable derivative of a cyclodextrin, including, but not limited to, the hydroxyalkyl derivatives of α-, β- and γ-cyclodextrin (especially the hydroxyethyl and hydroxypropyl derivatives of β-cyclodextrin and γ-cyclodextrin), randomly methylated β-cyclodextrin, sulfobutylether β-cyclodextrin, sulfobutylether γ-cyclodextrin, and the so-called branched β- and γ-cyclodextrin derivatives such as glucosyl-β-cyclodextrin and glucosyl-γ-cyclodextrin. The natural cyclodextrins are either used alone or in a mixture of two or more cyclodextrins, by way of non-limiting example, a mixture of the γ-cyclodextrin and the more water-soluble hydroxypropyl γ-cyclodextrin, or γ-cyclodextrin and sulfobutylether γ-cyclodextrin, or β-cyclodextrin and hydroxypropyl-β-cyclodextrin, or β-cyclodextrin and sulfobutylether β-cyclodextrin.

In some embodiments, a cyclodextrin in an ophthalmic solution of the invention is at a concentration of 0 to 20% w/v. In some embodiments, a cyclodextrin in an ophthalmic solution of the invention is at a concentration of 1 to 18% w/v, 1 to 16% w/v, 1 to 14% w/v, 2 to 12% w/v, 4 to 10% w/v, 5 to 9% w/v, or 6 to 8% w/v. In some embodiments, a cyclodextrin in an ophthalmic solution of the invention is at a concentration of about 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 16% w/v, 17% w/v, 18% w/v, 19% w/v, or 20% w/v.

In some embodiments, a pharmaceutically acceptable excipient in an ophthalmic solution of the invention is sulfobutylether-β-cyclodextrin, in particular at any of the specified concentrations and ranges of concentrations above, such as about 7% w/v. In some embodiments, a pharmaceutically acceptable excipient in an ophthalmic solution of the invention is hydroxypropyl-β-cyclodextrin, in particular at any of the specified concentrations and ranges of concentrations specified above, such as about 7% w/v. In some embodiments, reproxalap is at a concentration of about 0.25% w/v, and the cyclodextrin, such as sulfobutylether-β-cyclodextrin or hydroxypropyl-β-cyclodextrin, is at a concentration of about 7% w/v.

In some embodiments, a pharmaceutically acceptable excipient in an ophthalmic solution of the invention is sulfobutylether-β-cyclodextrin, in particular at any of the specified concentrations and ranges of concentrations above, such as about 11% w/v. In some embodiments, a pharmaceutically acceptable excipient in an ophthalmic solution of the invention is hydroxypropyl-β-cyclodextrin, in particular at any of the specified concentrations and ranges of concentrations specified above, such as about 11% w/v. In some embodiments, reproxalap is at a concentration of about 0.25% w/v, and the cyclodextrin, such as sulfobutylether-β-cyclodextrin or hydroxypropyl-β-cyclodextrin, is at a concentration of about 11% w/v.

In some embodiments, an ophthalmic solution of the invention comprises a pharmaceutically acceptable buffering agent. In some embodiments, a pharmaceutically acceptable buffering agent is a phosphate buffer, citrate buffer, tris buffer, histidine buffer or acetate buffer.

In some embodiments, a pharmaceutically acceptable buffering agent is sodium phosphate, dibasic. In some embodiments, a pharmaceutically acceptable buffering agent is sodium phosphate, monobasic. In some embodiments, a pharmaceutically acceptable buffering agent is a mixture of sodium phosphate, dibasic, and sodium phosphate, monobasic. In some embodiments, an ophthalmic solution of the invention comprises about 0.083% w/v sodium phosphate, dibasic, and about 0.017% w/v sodium phosphate, monobasic.

In some embodiments, the ophthalmic solution of the invention is at an approximately neutral pH. In some embodiments, an ophthalmic solution of the invention is at a pH of 6.5 to 8. In some embodiments, an ophthalmic solution of the invention is at a pH of 6.9 to 7.7. In some embodiments, an ophthalmic solution of the invention is at a pH of 7.1 to 7.5. In some embodiments, an ophthalmic solution of the invention is at a pH of about 7.3.

Pharmaceutically acceptable acids and/or bases may be used in the ophthalmic solution to adjust pH. In some embodiments, an ophthalmic solution of the invention comprises a pharmaceutically acceptable acid. In some embodiments, an ophthalmic solution of the invention comprises a pharmaceutically acceptable base. In some embodiments, an ophthalmic solution of the invention comprises a pharmaceutically acceptable acid and base. In some embodiments, the pharmaceutically acceptable acid is hydrochloric acid. In some embodiments, the pharmaceutically acceptable base is sodium hydroxide.

In some embodiments, an ophthalmic solution of the invention comprises a tonicity agent. In some embodiments, a tonicity agent is selected from the group consisting of dextrose, potassium chloride, propylene glycol, and sodium chloride. In some embodiments, an ophthalmic solution of the invention comprises a tonicity agent at a concentration of less than about 0.5% w/v. In some embodiments, an ophthalmic solution of the invention comprises a tonicity agent at a concentration of about 0.45%, 0.4%, 0.35%, 0.3%, 0.25%, 0.2%, 0.15%, or 0.1% w/v. In some embodiments, a tonicity agent is sodium chloride.

In some embodiments, the ophthalmic solution comprises reproxalap at the specified concentrations, cyclodextrin, phosphate, and sodium chloride. In some embodiments, the ophthalmic solution comprises reproxalap at the specified concentrations herein (e.g., 0.1% w/v, 0.25% w/v, 0.5% w/v, etc.), 5 to 9% w/v cyclodextrin (e.g., sulfobutylether-β-cyclodextrin or hydroxypropyl-β-cyclodextrin); 0.07% to 0.09% w/v sodium phosphate (dibasic), 0.015% to 0.19% w/v sodium phosphate (monobasic), and 0.2 to 0.3% w/v sodium chloride. In some embodiments, the ophthalmic solution comprises reproxalap at the specified concentrations herein (e.g., 0.1% w/v, 0.25% w/v, 0.5% w/v, etc.), about 7% w/v cyclodextrin (e.g., sulfobutylether-β-cyclodextrin or hydroxypropyl-β-cyclodextrin); 0.07% to 0.09% w/v sodium phosphate (dibasic), 0.015% to 0.019% w/v sodium phosphate (monobasic), and 0.2 to 0.3% w/v sodium chloride. In some embodiments, the ophthalmic solution is adjusted to an appropriate pH with sodium hydroxide or HCl.

In some embodiments, the ophthalmic solution comprises reproxalap at the specified concentrations, cyclodextrin, phosphate, and sodium chloride. In some embodiments, the ophthalmic solution comprises reproxalap at the specified concentrations herein (e.g., 0.1% w/v, 0.25% w/v, 0.5% w/v, etc.), 10 to 14% w/v cyclodextrin (e.g., sulfobutylether-β-cyclodextrin or hydroxypropyl-β-cyclodextrin); 0.07% to 0.09% w/v sodium phosphate (dibasic), 0.015% to 0.19% w/v sodium phosphate (monobasic), and 0.2 to 0.3% w/v sodium chloride. In some embodiments, the ophthalmic solution comprises reproxalap at the specified concentrations herein (e.g., 0.1% w/v, 0.25% w/v, 0.5% w/v, etc.), about 11% w/v cyclodextrin (e.g., sulfobutylether-β-cyclodextrin or hydroxypropyl-β-cyclodextrin); 0.07% to 0.09% w/v sodium phosphate (dibasic), 0.015% to 0.019% w/v sodium phosphate (monobasic), and 0.2 to 0.3% w/v sodium chloride. In some embodiments, the ophthalmic solution is adjusted to an appropriate pH with sodium hydroxide or HCl.

In some embodiments, the ophthalmic solution comprises the composition of 0.5% Reproxalap Ophthalmic Solution A in the Examples. In some embodiments, the ophthalmic solution comprises the composition of 0.5% Reproxalap Ophthalmic Solution B in the Examples. In some embodiments, the ophthalmic solution comprises the composition of 0.25% Reproxalap Ophthalmic Solution A in the Examples. In some embodiments, the ophthalmic solution comprises the composition of 0.25% Reproxalap Ophthalmic Solution (Basic) in the Examples.

4. Methods of Treatment

In one aspect, the present invention provides a method for treating allergic conjunctivitis in a subject, comprising topically administering to an eye of a subject in need thereof an ophthalmic solution of the invention. In some embodiments, the concentration of reproxalap in the ophthalmic solution used in the method is as described above.

In some embodiments, an ophthalmic solution of the invention can be administered at different frequencies suitable for effectively treating allergic conjunctivitis, for example, without causing severe or intolerable adverse effects.

In some embodiments, the allergic conjunctivitis for treatment is seasonal allergic conjunctivitis. In some embodiments, the allergic conjunctivitis for treatment is contact allergic conjunctivitis. In some embodiments, the allergic conjunctivitis for treatment is perennial conjunctivitis.

In some embodiments, an ophthalmic solution of the invention can be topically administered one (1) to twelve (12) times a day onto the eye. In some embodiments, an ophthalmic solution of the invention can be topically administered one (1) to ten (10) times a day onto the eye. In some embodiments, an ophthalmic solution of the invention can be topically administered one (1) to eight (8) times a day onto the eye. In some embodiments, an ophthalmic solution of the invention can be topically administered one (1) to six (6) times a day onto the eye. In some embodiments, an ophthalmic solution of the invention can be topically administered one (1) to four (4) times a day onto the eye.

In some embodiments, a method of the invention comprises topically administering an ophthalmic solution of the invention up to twelve times a day. In some embodiments, a method of the invention comprises topically administering an ophthalmic solution of the invention up to eleven times a day. In some embodiments, a method of the invention comprises topically administering an ophthalmic solution of the invention up to ten times a day. In some embodiments, a method of the invention comprises topically administering an ophthalmic solution of the invention up to nine times a day. In some embodiments, a method of the invention comprises topically administering an ophthalmic solution of the invention up to eight times a day. In some embodiments, a method of the invention comprises topically administering an ophthalmic solution of the invention up to seven times a day. In some embodiments, a method of the invention comprises topically administering an ophthalmic solution of the invention six times a day. In some embodiments, a method of the invention comprises topically administering an ophthalmic solution of the invention five times a day. In some embodiments, a method of the invention comprises topically administering an ophthalmic solution of the invention four times a day (QID). In some embodiments, a method of the invention comprises topically administering an ophthalmic solution of the invention three times a day (TID). In some embodiments, a method of the invention comprises topically administering an ophthalmic solution of the invention two times a day (BID). In some embodiments, a method of the invention comprises topically administering an ophthalmic solution of the invention once a day (QD). In some embodiments, a method of the invention comprises topically administering an ophthalmic solution of the invention as needed (PRN).

In some embodiments, the present invention provides a method for treating allergic conjunctivitis in a subject, comprising topically administering to an eye of the subject an ophthalmic solution of the invention. In some embodiments, a method of the invention comprises topically administering an ophthalmic solution of the invention four times a day (QID). In some embodiments, a method of the invention comprises topically administering an ophthalmic solution of the invention three times a day (TID). In some embodiments, a method of the invention comprises topically administering an ophthalmic solution of the invention two times a day (BID). In some embodiments, a method of the invention comprises topically administering an ophthalmic solution of the invention once a day (QD). In some embodiments, a method of the invention comprises topically administering an ophthalmic solution of the invention as needed (PRN).

In some embodiments, a method of treating allergic conjunctivitis comprises topically administering to an eye of a subject in need thereof an ophthalmic solution of the invention four times a day (QID), three times a day (TID), two times a day (BID), once a day (QD), followed by administration as needed by the subject (PRN). In some embodiments, a method of treating allergic conjunctivitis comprises topically administering an ophthalmic solution of the invention four times a day (QID) followed by administration as needed (PRN).

In some embodiments, a method of treating allergic conjunctivitis comprises topically administering to an eye of a subject in need thereof an ophthalmic solution of the invention prior to an expected or certain exposure to an eye allergen. In some embodiments, the ophthalmic solution is topically administered to an eye within the time period of durability of the therapeutic effect, e.g., for a 0.25% w/v or 0.5% w/v reproxalap solution, prior to an expected or certain exposure to an eye allergen. In some embodiments, an ophthalmic solution of the invention is administered 3.5 h or less, 3 h or less, 2.5 h or less, 2 h or less, 1.5 h or less, 1 h or less, 0.5 h or less, 25 min or less, 20 min or less, 25 min or less, 20 min or less, 15 min or less, 10 min or less, or 5 min or less prior to an expected or certain exposure to an eye allergen, or immediately prior to exposure to an eye allergen. In some embodiments, an ophthalmic solution of the invention is administered 1.5 h or less, 1 h or less, 0.5 h or less, 25 min or less, 20 min or less, 25 min or less, 20 min or less, 15 min or less, 10 min or less, or 5 min or less prior to an expected or certain exposure to an eye allergen. In some embodiments, an ophthalmic solution of the invention is administered 0-0.5 h, 0-1 h, 0-1.5 h, 0-2 h, 0-2.5 h, 0-3 h, 0-3.5 h prior to an expected or certain exposure to an eye allergen. In some embodiments, an ophthalmic solution of the invention is administered 0.5-1 h, 0.5-1.5 h, 0.5-2 h, 0.5-2.5 h, 0.5-3 h, 0.5-3.5 h prior to an expected or certain exposure to an eye allergen. In some embodiments, an ophthalmic solution of the invention is administered 1-1.5 h, 1-2 h, 1-2.5 h, 1-3 h, or 1-3.5 h prior to an expected or certain exposure to an eye allergen. In some embodiments, an ophthalmic solution of the invention is administered 1.5-2 h, 1.5-2.5 h, 1.5-3 h, 1.5-3.5 h prior to an expected or certain exposure to an eye allergen. In some embodiments, an ophthalmic solution of the invention is administered –2.5 h, 2-3 h, 2-3.5 h prior to an expected or certain exposure to an eye allergen. In some embodiments, an ophthalmic solution of the invention is administered 2.5-3 h or 2.5-3.5 h prior to an expected or certain exposure to an eye allergen.

In some embodiments, a method for treating allergic conjunctivitis comprises topically administering to an eye of a subject in need thereof an ophthalmic solution of the invention one time, up to two times, up to three times, up to four times, up to five times, up to six times, up to seven times, or up to eight times prior to an expected or certain exposure to an eye allergen. In some embodiments, a method for treating allergic conjunctivitis comprises topically administering to an eye of a subject in need thereof an ophthalmic solution of the invention one time, two times, three times, four times, five times, six times, seven times, or eight times prior to an expected or certain exposure to an eye allergen. In some embodiments, the ophthalmic solution when administered two or more times is administered over 3.5 h, 3 h, 2.5 h, 2 h, 1.5 h, 1 h, or 0.5 h period before an expected or certain exposure to an eye allergen. In some embodiments, the ophthalmic solution when administered one time is administered 1.5 h or less, 1 h or less, 0.5 h or less, 25 min or less, 20 min or less, 25 min or less, 20 min or less, 15 min or less, 10 min or less, or 5 min or less prior to an expected or certain exposure to an eye allergen, or immediately prior to exposure to an expected or certain exposure to an eye allergen. In some embodiments, each time of administration of the ophthalmic solution is with one or two doses (e.g., drops) of the ophthalmic solution. In some embodiments, each time of administration of the ophthalmic solution is with a single dose (e.g., one drop) of the ophthalmic solution.

In some embodiments, the subject for treatment selected for treatment prior to an expected or certain exposure to an eye allergen has a history of allergic conjunctivitis. In some embodiments, the subject selected for treatment prior to an expected or certain exposure to an eye allergen has a history of allergic conjunctivitis and has a positive allergen skin test for one or more eye allergens, in particular for the eye allergen to which the subject is expected to be exposed. In some embodiments, the subject selected for treatment prior to an expected or certain exposure to an eye allergen has been previously clinically diagnosed with allergic conjunctivitis. In some embodiments, the subject selected for treatment prior to an expected or certain exposure to an eye allergen has been previously clinically diagnosed with allergic conjunctivitis and has a positive allergen skin test for one or more eye allergens, in particular for the eye allergen to which the subject is expected to be exposed. For the allergen skin test, a panel of allergens, particularly airborne allergens can be used, including allergens such as Hazel (e.g., *Corylus avellana*), Alder (e.g., *Alnus incana*), Birch (e.g., *Betula alba*), Plane (e.g., *Platanus vulgaris*), Cypress (e.g., *Cupressus sempervirens*), Grass mix (e.g., smooth meadow grass/*Poa pratensis*, cock's foot grass/*Dactilis glomerata*, perennial rye grass/*Lolium perenne*, timothy grass/*Phleum pratense*, meadow fescue/*Festuca pratensis*, meadow oat grass/*Helictotrichon pretense*), Olive (e.g., *Olea europaea*), Mugwort (e.g., *Artemisia vulgaris*), Ragweed (e.g., *Ambrosia artemisiifolia*), Alternaria (e.g., *Alternaria alternata* (*tenuis*)), Cladosporium (e.g., *Cladosporium herbarum*), Aspergillus (e.g., *Aspergillus fumigatus*), Parietaria (e.g., *Parietaria*), Cat, Dog, *Dermatophagoides pteronyssinus*, *Dermatophagoides farina*, and *Blatella* (e.g., *Blatella germanica*).

In some embodiments, a method for treating allergic conjunctivitis in a subject comprises administering to an eye of a subject in need thereof an ophthalmic solution of the invention at or after exposure to the eye allergen. In some embodiments, a method for treating allergic conjunctivitis in a subject comprises administering an ophthalmic solution of the invention to an eye of a subject in need thereof immediately after exposure to an eye allergen. In some embodiments, a method for treating allergic conjunctivitis comprises administering to an eye of a subject in need thereof an ophthalmic solution of the invention at or after the onset of symptoms of allergic conjunctivitis. In some embodiments, a method for treating allergic conjunctivitis comprises administering to an eye of a subject in need thereof an ophthalmic solution of the invention immediately after the onset of symptoms of allergic conjunctivitis. In some embodiments, a method for treating allergic conjunctivitis comprises administering to an eye of a subject in need thereof an ophthalmic solution of the invention prior to reaching highest severity of symptoms of allergic conjunctivitis. In some embodiments, the severity of symptoms of allergic conjunctivitis can use the scoring for ocular itch, conjunctival redness, and ocular tearing used in the Examples below or as is known in the art. In some embodiments, the scoring for severity of symptoms of allergic conjunctivitis are described in Ciolino et al., Clinical Ophthalmology, 2015, 9:765-772; Abelson et al., J Ocular Pharmacol., 1998, 14(6):533-542; and McLaurin et al., Clinical Sci., 2015, 34(10):1245-1251; all publications incorporated by reference herein). In some embodiments, the treatment at or after exposure to the eye allergen and/or after the onset of symptoms of allergic conjunctivitis can further include an initiation phase, exacerbation phase, and/or maintenance phase, as further discussed herein.

In some embodiments, a method for treating allergic conjunctivitis in a subject comprises administering to an eye of a subject in need thereof an ophthalmic solution of the invention by 5 min or less, 10 min or less, 15 min or less, 20 min or less, 25 min or less, 30 min or less, 35 min or less, 40 min or less, 45 min or less, 50 min or less, 60 min (1 h) or less, 75 min (1.25 h) or less, 90 min (1.5 h) or less, 105 min (1.75 h) or less, or 120 min (2 h) or less after exposure to an eye allergen or after the onset of symptoms of allergic conjunctivitis. In some embodiments, a method for treating allergic conjunctivitis in a subject comprises administering to an eye of a subject in need thereof an ophthalmic solution of the invention by 5 min or less, 10 min or less, 15 min or less, 20 min or less, 25 min or less, 30 min or less, 35 min or less, 40 min or less, 45 min or less, 50 min or less, 60 min (1 h) or less, 75 min (1.25 h) or less, or 90 min (1.5 h) or less after exposure to an eye allergen or after the onset of symptoms of allergic conjunctivitis. In some embodiments of the method, an ophthalmic solution of the invention is administered about 0-5 min, 0-10 min, 0-15 min, 0-20 min, 0-25 min, 0-30 min, 0-35 min, 0-40 min, 0-45 min, 0-50 min, 0-60 min, 0-75 min, 0-90 min, 0-105 min, or 0-120 min following exposure to an eye allergen or after the onset of symptoms of allergic conjunctivitis. In some embodiments of the method, an ophthalmic solution of the invention is administered about 5-10 min, 5-15 min, 5-20 min, 5-25 min, 5-30 min, 5-35 min, 5-40 min, 5-45 min, 5-50 min, 5-60 min, 5-75 min, 5-90 min, 5-105 min, or 5-120 min after exposure to an eye allergen or after the onset of symptoms of allergic conjunctivitis. In some embodiments of the method, an ophthalmic solution of the invention is administered about 10-15 min, 10-20 min, 10-25 min, 10-30 min, 10-35 min, 10-40 min, 10-45 min, 10-50 min, 10-60 min, 10-75 min, 10-90 min, 10-105 min, or 10-120 min after exposure to an eye allergen or after the onset of symptoms of allergic conjunctivitis. In some embodiments of the method, an ophthalmic solution of the invention is administered within 15-20 min, 15-25 min, 15-30 min, 15-35 min, 15-40 min, 15-45 min, 15-50 min, 15-60 min, 15-75 min, 15-90 min, 15-105 min, or 15-120 min after exposure to an eye allergen or after the onset of symptoms of allergic conjunctivitis. In some embodiments of the method, an ophthalmic solution of the invention is administered by 20-25 min, 20-30 min, 20-35 min, 20-40 min, 20-45 min, 20-50 min, 20-60 min, 20-75 min, 20-90 min, 20-105 min, or 20-120 min after exposure to an eye allergen or after the onset of symptoms of allergic conjunctivitis. In some embodiments of the method, an ophthalmic solution of the invention is administered by 25-30 min, 25-35 min, 25-40 min, 25-45 min, 25-50 min, 25-60 min, 25-75 min, 25-90 min, 25-105 min, or 25-120 min after exposure to an eye allergen or after the onset of symptoms of allergic conjunctivitis. In some embodiments of the method, an ophthalmic solution of the invention is administered by 30-35 min, 30-40 min, 30-45 min, 30-50 min, 30-60 min, 30-75 min, 30-90 min, 30-105 min, or 30-120 min after exposure to an eye allergen or after the onset of symptoms of allergic conjunctivitis. In some embodiments of the method, an ophthalmic solution of the invention is administered by 35-40 min, 35-45 min, 35-50 min, 35-60 min, 35-75 min, 35-90 min, 35-105 min, or 35-120 min after exposure to an eye allergen or after the onset of symptoms of allergic conjunctivitis. In some embodiments of the method, an ophthalmic solution of the invention is administered by 40-45 min, 40-50 min, 40-60 min, 40-75 min, 40-90 min, 40-105 min, or 40-120 min after exposure to an eye allergen or after the onset of symptoms of allergic conjunctivitis. In some embodiments of the method, an ophthalmic solution of the invention is administered by 45-50 min, 45-60 min, 45-75 min, 45-90 min, 45-105 min, or 45-120 min after exposure to an eye allergen or after the onset of symptoms of allergic conjunctivitis. In some embodiments of the method, an ophthalmic solution of the invention is administered by 50-60 min, 50-75 min, 50-90 min, 50-105 min, or 50-120 min after exposure to an eye allergen or after the onset of symptoms of allergic conjunctivitis. In some embodiments of the method, an ophthalmic solution of the invention is administered by 60-75 min, 60-90 min, 60-105 min, or 60-120 min after exposure to an eye allergen or after the onset of symptoms of allergic conjunctivitis. In some embodiments of the method, an ophthalmic solution of the invention is administered by 75-90 min, 75-105 min, or 75-120 min following exposure to an eye allergen or after the onset of symptoms of allergic conjunctivitis. In some embodiments of the method, an ophthalmic solution of the invention is administered by 90-105 min or 90-120 min after exposure to an eye allergen or after the onset of symptoms of allergic conjunctivitis.

In some embodiments, a method for treating allergic conjunctivitis in a subject comprises topically administering to an eye of a subject in need thereof an ophthalmic solution of the invention at or after exposure to an eye allergen, or at or after onset of symptoms of allergic conjunctivitis, where the ophthalmic solution is administered up to twelve times a day, up to eleven times a day, up to ten times a day, up to nine times a day, up to eight times a day, up to seven times a day, up to six times a day, up to five times a day, up to four times a day, up to three times a day, up to two times a day, or once a day. In some embodiments, a method for treating allergic conjunctivitis in a subject comprises topically administering to an eye of a subject in need thereof an ophthalmic solution of the invention at or after exposure to an eye allergen, or at or after onset of symptoms of allergic conjunctivitis, where the ophthalmic solution is administered twelve times a day, eleven times a day, ten times a day, nine times a day, eight times a day, seven times a day six times a day, five times a day, four times a day (QID), three times a day (TID), two times a day (BID), once a day (QD). In some embodiments, a method for treating allergic conjunctivitis in a subject comprises topically administering to any eye of a subject in need thereof an ophthalmic solution of the invention at or after exposure to an eye allergen, or after onset of symptoms of allergic conjunctivitis, where the ophthalmic solution is administered as needed (PRN). In some embodiments, a method for treating allergic conjunctivitis in a subject comprises topically administering to an eye of a subject in need thereof an ophthalmic solution of the invention at or after exposure to an eye allergen, or at or after onset of symptoms of allergic conjunctivitis, where the ophthalmic solution is administered four times a day (QID), three times a day (TID), two times a day (BID), once a day (QD), or as needed (PRN). In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where the ophthalmic solution is administered six times a day, five times a day, four times a day (QID), three times a day (TID), two times a day (BID), once a day (QD), followed by administration as needed (PRN). In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where the ophthalmic solution is administered four times a day (QID), three times a day (TID), two times a day (BID), once a day (QD), followed by administration as needed by the subject (PRN). In some embodiments, an ophthalmic solution of the invention is administered four times a day (QID) followed by administration as needed (PRN).

In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where each time of administration is every 1 h, 1.5 h, 2 h, 2.5 h, 3 h, 3.5 h, or 4 h. In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where each time of administration is every 1-1.5 h, 1-2 h, 1-2.5 h, 1-3 h, 1-3.5 h, or 1-4 h. In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where each time of administration is every 1.5-2 h, 1.5-2.5 h, 1.5-3 h, 1.5-3.5 h, or 1.5-4 h. In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where each time of administration is every 2-2.5 h, 2-3 h, 2-3.5 h, or 2-4 h. In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, where each time of administration is every 3-3.5 h or 3-4 h.

In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, wherein the ophthalmic solution is administered two (2) times a day (BID), and each time of administration is 60 min (1 h) apart; 90 min (1.5 h) apart; 120 min (2 h) apart; 150 min (2.5 h) apart; 180 min (3 h) apart; 210 min (3.5 h) apart; or 240 min (4 h) apart. In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, wherein the ophthalmic solution is administered three (3) times a day (TID) and each time of administration is 60 min (1 h) apart; 90 min (1.5 h) apart; 120 min (2 h) apart; 150 min (2.5 h) apart; 180 min (3 h) apart; 210 min (3.5 h) apart; or 240 min (4 h) apart. In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, wherein the ophthalmic solution is administered four (4) times a day (QID) and each time of administration is 60 min (1 h) apart; 90 min (1.5 h) apart; 120 min (2 h) apart; 150 min (2.5 h) apart; 180 min (3 h) apart; 210 min (3.5 h) apart; or 240 min (4 h) apart. In some embodiments, a method for treating allergic conjunctivitis comprises topically administering to an eye of a subject in need thereof an ophthalmic solution of the invention at or after exposure to an eye allergen, or at or after onset of symptoms of allergic conjunctivitis, wherein the ophthalmic solution is administered two (2) times a day (BID), and each time of administration is 60 min (1 h) apart; 90 min (1.5 h) apart; or 120 min (2 h) apart.

In some embodiments, each time of administration of the ophthalmic solution at or after exposure to an eye allergen, or at or after onset of symptoms of allergic conjunctivitis is with one or two doses (e.g., drops) of the ophthalmic solution. In some embodiments, each time of administration of the ophthalmic solution is with a single dose (e.g., one drop) of the ophthalmic solution. In some embodiments, each time of administration of the ophthalmic solution is with two doses (e.g., two drops) of the ophthalmic solution.

In some embodiments, the subject for treatment selected for treatment at or after exposure to an eye allergen, or at or after onset of symptoms of allergic conjunctivitis has a history of allergic conjunctivitis. In some embodiments, the subject selected for treatment at or after exposure to an eye allergen, or at or after onset of symptoms of allergic conjunctivitis has a history of allergic conjunctivitis and has a positive allergen skin test for one or more eye allergens, in particular for the eye allergen to which the subject is expected to be exposed. In some embodiments, the subject selected for treatment at or after exposure to an eye allergen, or at or after onset of symptoms of allergic conjunctivitis has been previously clinically diagnosed with allergic conjunctivitis. In some embodiments, the subject selected for treatment at or after exposure to an eye allergen, or at or after onset of symptoms of allergic conjunctivitis has been previously clinically diagnosed with allergic conjunctivitis and has a positive allergen skin test for one or more eye allergens, in particular for the eye allergen to which the subject is expected to be exposed. In some embodiments, a standard allergen skin test employs a panel of allergens, such as that described above.

In some embodiments, a method for treating allergic conjunctivitis comprises administering to an eye of a subject in need thereof an ophthalmic solution of the invention prior to an expected or certain exposure to an eye allergen, and further comprising administering an ophthalmic solution of the invention at or after exposure to the eye allergen, or at or after onset of symptoms of allergic conjunctivitis. This treatment protocol provides a two phased treatment regimen, the first phase being administration prior to an expected or certain exposure to an eye allergen, and a second phase being administration at or after exposure of an eye allergen, or at or after the onset of symptoms of eye allergy. In some embodiments, a method for treating allergic conjunctivitis comprises a first treatment phase comprising administering the ophthalmic solution prior to an expected or certain exposure of the subject to an eye allergen; and a second treatment phase comprising administering the ophthalmic solution at or after exposure of the subject to an eye allergen, or at or after onset of symptoms of allergic conjunctivitis. In some embodiments, the second phase of treatment can further include treatment in an initiation phase, exacerbation phase, and/or maintenance phase, as discussed herein.

In some embodiments, in the first treatment phase (administering to an eye of a subject in need thereof an ophthalmic solution of the invention prior to an expected or certain exposure to an eye allergen), an ophthalmic solution is topically administered to an eye within the time period of durability of the therapeutic effect, e.g., for a 0.25% w/v or 0.5% w/v reproxalap solution, prior to an expected or certain exposure to an eye allergen. In some embodiments, in the first treatment phase, an ophthalmic solution of the invention is administered 3.5 h or less, 3 h or less, 2.5 h or less, 2 h or less, 1.5 h or less, 1 h or less, 0.5 h or less, 25 min or less, 20 min or less, 25 min or less, 20 min or less, 15 min or less, 10 min or less, or 5 min or less prior to an expected or certain exposure to an eye allergen, or immediately prior to exposure to an eye allergen. In some embodiments, an ophthalmic solution of the invention is administered 0-0.5 h, 0-1 h, 0-1.5 h, 0-2 h, 0-2.5 h, 0-3 h, 0-3.5 h prior to an expected or certain exposure to an eye allergen. In some embodiments, an ophthalmic solution of the invention is administered 0.5-1 h, 0.5-1.5 h, 0.5-2 h, 0.5-2.5 h, 0.5-3 h, 0.5-3.5 h prior to an expected or certain exposure to an eye allergen. In some embodiments, an ophthalmic solution of the invention is administered 1-1.5 h, 1-2 h, 1-2.5 h, 1-3 h, 1-3.5 h prior to an expected or certain exposure to an eye allergen. In some embodiments, an ophthalmic solution of the invention is administered 1.5-2 h, 1.5-2.5 h, 1.5-3 h, 1.5-3.5 h prior to an expected or certain exposure to an eye allergen. In some embodiments, an ophthalmic solution of the invention is administered 2-2.5 h, 2-3 h, 2-3.5 h prior to an expected or certain exposure to an eye allergen. In some embodiments, an ophthalmic solution of the invention is administered 2.5-3 h or 2.5-3.5 h prior to an expected or certain exposure to an eye allergen.

In some embodiments, in the first treatment phase (administering to an eye of a subject in need thereof an ophthalmic solution of the invention prior to an expected or certain exposure to an eye allergen), an ophthalmic solution of the invention is administered one time, up to two times, up to three times, up to four times, up to five times, up to six times, up to seven times, or up to eight times prior to an expected or certain exposure to an eye allergen. In some embodiments, in the first treatment phase, an ophthalmic solution of the invention is administered one time, two times, three times, four times, five times, six times, seven times, or eight times prior to an expected or certain exposure to an eye allergen. In some embodiments, in the first treatment phase, an ophthalmic solution of the invention is administered one time, up to two times, up to three times, or up to four times prior to an expected or certain exposure to an eye allergen. In some embodiments, in the first treatment phase, an ophthalmic solution of the invention is administered one time, two times, three times, or four times prior to an expected or certain exposure to an eye allergen. In some embodiments, the ophthalmic composition when administered two or more times is administered over 3.5 h, 3 h, 2.5 h, 2 h, 1.5 h, 1 h, or 0.5 h before an expected or certain exposure to an eye allergen. In some embodiments of the first treatment phase, the ophthalmic solution when administered one time is administered 1.5 h or less, 1 h or less, 0.5 h or less, 25 min or less, 20 min or less, 25 min or less, 20 min or less, 15 min or less, 10 min or less, or 5 min or less prior to an expected or certain exposure to an eye allergen, or immediately prior to exposure to an expected or certain exposure to an eye allergen. In some embodiments, each time of administration of the ophthalmic solution in the first treatment phase is with one or two doses (e.g., drops) of the ophthalmic solution. In some embodiments, each time of administration of the ophthalmic solution in the first treatment phase is with a single dose (e.g., one drop) of the ophthalmic solution). In some embodiments, each time of administration of the ophthalmic solution in the first treatment phase is with two doses (e.g., two drops) of the ophthalmic solution.

In some embodiments, in the second treatment phase (administering to an eye of a subject in need thereof an ophthalmic solution of the invention in the period at or after exposure to an eye allergen, or at or after onset of symptoms of allergic conjunctivitis), an ophthalmic solution of the invention is administered within 5 min, 10 min, 15 min, 20 min, 25 min, 30 min, 35 min, 40 min, 45 min, 50 min, 60 min (1 h), 75 min (1.25 h), 90 min (1.5 h), 105 min (1.75 h), or 120 min (2 h) after the exposure to an eye allergen or after the onset of symptoms of allergic conjunctivitis. In some embodiments, in the second treatment phase, an ophthalmic solution of the invention is administered within 0-5 min, 0-10 min, 0-15 min, 0-20 min, 0-25 min, 0-30 min, 0-35 min, 0-40 min, 0-45 min, 0-50 min, 0-60 min, 0-75 min, 0-90 min, 0-105 min, or 0-120 min following exposure to an eye allergen or after the onset of symptoms of allergic conjunctivitis. In some embodiments of the method, an ophthalmic solution of the invention is administered within 5-10 min, 5-15 min, 5-20 min, 5-25 min, 5-30 min, 5-35 min, 5-40 min, 5-45 min, 5-50 min, 5-60 min, 5-75 min, 5-90 min, 5-105 min, or 5-120 min following exposure to an eye allergen or after the onset of symptoms of allergic conjunctivitis. In some embodiments of the method, an ophthalmic solution of the invention is administered within 10-15 min, 10-20 min, 10-25 min, 10-30 min, 10-35 min, 10-40 min, 10-45 min, 10-50 min, 10-60 min, 10-75 min, 10-90 min, 10-105 min, or 10-120 min after exposure to an eye allergen or after the onset of symptoms of allergic conjunctivitis. In some embodiments of the method, an ophthalmic solution of the invention is administered within 15-20 min, 15-25 min, 15-30 min, 15-35 min, 15-40 min, 15-45 min, 15-50 min, 15-60 min, 15-75 min, 15-90 min, 15-105 min, or 15-120 min following exposure to an eye allergen or after the onset of symptoms of allergic conjunctivitis. In some embodiments of the method, an ophthalmic solution of the invention is administered within 20-25 min, 20-30 min, 20-35 min, 20-40 min, 20-45 min, 20-50 min, 20-60 min, 20-75 min, 20-90 min, 20-105 min, or 20-120 min following exposure to an eye allergen or after the onset of symptoms of allergic conjunctivitis. In some embodiments of the method, an ophthalmic solution of the invention is administered within 25-30 min, 25-35 min, 25-40 min, 25-45 min, 25-50 min, 25-60 min, 25-75 min, 25-90 min, 25-105 min, or 25-120 min following exposure to an eye allergen or after the onset of symptoms of allergic conjunctivitis. In some embodiments of the method, an ophthalmic solution of the invention is administered within 30-35 min, 30-40 min, 30-45 min, 30-50 min, 30-60 min, 30-75 min, 30-90 min, 30-105 min, or 30-120 min following exposure to an eye allergen or after the onset of symptoms of allergic conjunctivitis. In some embodiments of the method, an ophthalmic solution of the invention is administered within 35-40 min, 35-45 min, 35-50 min, 35-60 min, 35-75 min, 35-90 min, 35-105 min, or 35-120 min following exposure to an eye allergen or after the onset of symptoms of allergic conjunctivitis. In some embodiments of the method, an ophthalmic solution of the invention is administered within 40-45 min, 40-50 min, 40-60 min, 40-75 min, 40-90 min, 40-105 min, or 40-120 min following exposure to an eye allergen or after the onset of symptoms of allergic conjunctivitis. In some embodiments of the method, an ophthalmic solution of the invention is administered within 45-50 min, 45-60 min, 45-75 min, 45-90 min, 45-105 min, or 45-120 min following exposure to an eye allergen or after the onset of symptoms of allergic conjunctivitis. In some embodiments of the method, an ophthalmic solution of the invention is administered within 50-60 min, 50-75 min, 50-90 min, 50-105 min, or 50-120 min following exposure to an eye allergen or after the onset of symptoms of allergic conjunctivitis. In some embodiments of the method, an ophthalmic solution of the invention is administered within 60-75 min, 60-90 min, 60-105 min, or 60-120 min following exposure to an eye allergen or after the onset of symptoms of allergic conjunctivitis. In some embodiments of the method, an ophthalmic solution of the invention is administered within 75-90 min, 75-105 min, or 75-120 min following exposure to an eye allergen or after the onset of symptoms of allergic conjunctivitis. In some embodiments of the method, an ophthalmic solution of the invention is administered within 90-105 min, or 90-120 min following exposure to an eye allergen or after the onset of symptoms of allergic conjunctivitis.

In some embodiments, in the second treatment phase, an ophthalmic solution of the invention is administered up to eight times a day, up to seven times a day, up to six times a day, up to five times a day, up to four times a day, up to three times a day, up to two times a day, or once a day. In some embodiments, in the second treatment phase, an ophthalmic solution of the invention is administered eight times a day, seven times a day, six times a day, five times a day, four times a day (QID), three times a day (TID), two times a day (BID), or once a day (QD). In some embodiments, in the second treatment phase, an ophthalmic solution of the invention is administered as needed (PRN). In some embodiments, in the second treatment phase, an ophthalmic solution of the invention is administered eight times a day, seven times a day, six times a day, five times a day, four times a day (QID), three times a day (TID), two times a day (BID), once a day (QD), followed by administration as needed (PRN). In some embodiments of the method, an ophthalmic solution of the invention is administered four times a day (QID) followed by administration as needed (PRN).

In some embodiments, in the second treatment phase, each time of administration is every 1 h, 1.5 h, 2 h, 2.5 h, 3 h, 3.5 h, or 4 h. In some embodiments of the method each time of administration is every 1-1.5 h, 1-2 h, 1-2.5 h, 1-3 h, 1-3.5 h, or 1-4 h. In some embodiments of the method, each time of administration is every 1.5-2 h, 1.5-2.5 h, 1.5-3 h, 1.5-3.5 h, or 1.5-4 h. In some embodiments of the method, each time of administration is every 2-2.5 h, 2-3 h, 2-3.5 h, or 2-4 h. In some embodiments of the method, each time of administration is every 3-3.5 h or 3-4 h.

In some embodiments, in the second treatment phase, an ophthalmic solution of the invention is administered two (2) times a day (BID), and each time of administration is 60 min (1 h) apart; 90 min (1.5 h) apart; 120 min (2 h) apart; 150 min (2.5 h) apart; 180 min (3 h) apart; 210 min (3.5 h) apart; or 240 min (4 h) apart. In some embodiments of the method, an ophthalmic solution of the invention is administered three (3) times a day (TID) and each time of administration is 60 min (1 h) apart; 90 min (1.5 h) apart; 120 min (2 h) apart; 150 min (2.5 h) apart; 180 min (3 h) apart; 210 min (3.5 h) apart; or 240 min (4 h) apart. In some embodiments of the method, an ophthalmic solution of the invention is administered four (4) times a day (QID) and each time of administration is 60 min (1 h) apart; 90 min (1.5 h) apart; 120 min (2 h) apart; 150 min (2.5 h) apart; 180 min (3 h) apart; 210 min (3.5 h) apart; or 240 min (4 h) apart. In some embodiments of the method, an ophthalmic solution of the invention is administered two (2) times a day (BID), and each time of administration is 60 min (1 h) apart; 90 min (1.5 h) apart; or 120 min (2 h) apart.

In some embodiments, in the second treatment phase, each time of administration of the ophthalmic solution at or after exposure to an eye allergen, or at or after onset of symptoms of allergic conjunctivitis is with one or two doses (e.g., drops) of the ophthalmic solution. In some embodiments, in the second treatment phase, each time of administration of the ophthalmic solution is with a single dose (e.g., one drop) of the ophthalmic solution. In some embodiments, in the second treatment phase, each time of administration of the ophthalmic solution is with two doses (e.g., two drops) of the ophthalmic solution.

In some embodiments, in the method for treating allergic conjunctivitis comprising a first treatment phase and a second treatment phase, wherein the first treatment phase comprises administering the ophthalmic solution prior to an expected or certain exposure of the subject to an eye allergen; and the second treatment phase comprises administering the ophthalmic solution at or after exposure of the subject to an eye allergen, or at or after onset of symptoms of allergic conjunctivitis, the subject selected for treatment has a history of allergic conjunctivitis. In some embodiments, the subject selected for treatment has a history of allergic conjunctivitis and has a positive allergen skin test for one or more eye allergens, in particular for the eye allergen to which the subject is expected to be exposed. In some embodiments, the subject selected for treatment has been previously clinically diagnosed with allergic conjunctivitis. In some embodiments, the subject selected for treatment has been previously clinically diagnosed with allergic conjunctivitis and has a positive allergen skin test for one or more eye allergens, in particular for the eye allergen to which the subject is expected to be exposed. In some embodiments, a standard allergen skin test employs a panel of allergens, such as that described above.

In some embodiments, a method of the invention comprises topically administering an ophthalmic solution of the invention at various strengths (for example, at different reproxalap concentrations and different administration frequencies, as described herein).

In some embodiments, a method of the invention comprises topically administering an ophthalmic solution comprising about 0.25% w/v reproxalap, or a pharmaceutically acceptable salt thereof, four times a day, three times a day, or two times a day.

In some embodiments, a method of the invention comprises topically administering an ophthalmic solution comprising about 0.30% w/v reproxalap, or a pharmaceutically acceptable salt thereof, four times a day, three times a day, or two times a day.

In some embodiments, a method of the invention comprises topically administering an ophthalmic solution comprising about 0.35% w/v reproxalap, or a pharmaceutically acceptable salt thereof, four times a day, three times a day, or two times a day.

In some embodiments, a method of the invention comprises topically administering an ophthalmic solution comprising about 0.4% w/v reproxalap, or a pharmaceutically acceptable salt thereof, four times a day, three times a day, or two times a day.

In some embodiments, a method of the invention comprises topically administering an ophthalmic solution comprising about 0.45% w/v reproxalap, or a pharmaceutically acceptable salt thereof, four times a day, three times a day, or two times a day.

In some embodiments, a method of the invention comprises topically administering an ophthalmic solution comprising about 0.5% w/v reproxalap, or a pharmaceutically acceptable salt thereof, four times a day, three times a day, or two times a day.

In some embodiments, a method of the invention comprises topically administering an ophthalmic solution comprising 0.3% to 0.4% w/v reproxalap, or a pharmaceutically acceptable salt thereof, four times a day, three times a day, or two times a day.

In some embodiments, a method of the invention comprises topically administering an ophthalmic solution comprising 0.2% to 0.4% w/v reproxalap, or a pharmaceutically acceptable salt thereof, four times a day, three times a day, or two times a day.

In some embodiments, a method of the invention comprises treatment at two or more phases, including an initiation phase, exacerbation phase, and/or maintenance phase. In some embodiments, the treatments at the different phases can include administration of different strengths of reproxalap, different frequency of administration, or a combination of different strengths of reproxalap and different frequencies of administration. In some embodiments, the initiation phase of treatment is started at the onset of symptoms of allergic conjunctivitis. In some embodiments, the initiation phase of treatment is started when allergic conjunctivitis symptoms are at exacerbation of disease signs and/or symptoms. In some embodiments, the treatment in the initiation phase and/or exacerbation phase can be up to 1 week, up to 2 weeks, up to 3 weeks, up to 4 weeks, up to 6 weeks, up to 8 weeks, or up to 12 weeks. In some embodiments, the maintenance phase can be up to 1 week, up to 2 weeks, up to 3 weeks, up to 4 weeks, up to 6 weeks, up to 8 weeks, or up to 12 weeks or more, e.g., until symptoms of allergic conjunctivitis lessen or are resolved.

In some embodiments, a method of the invention comprises two or more phases, wherein an ophthalmic solution of the invention is topically administering at different strengths in different phases. In some embodiments, a method of the invention comprises an initiation phase and a maintenance phase, wherein the ophthalmic solution is topically administered at a higher strength in the initiation phase than in the maintenance phase. In some embodiments, a treatment cycle of a method of the invention comprising multiple phases, including an exacerbation phase during which signs and/or symptoms become worse.

In some embodiments, the method of the invention comprises two or more phases, wherein an ophthalmic solution of the invention is topically administering at different strengths in different phases. In some embodiments, a method of the invention comprises an initiation phase, wherein the ophthalmic solution is topically administered at a high strength in the initiation phase, at a low strength in the maintenance phase, and at a high strength during an exacerbation of disease signs and/or symptoms.

In some embodiments, an ophthalmic solution administered in an initiation phase comprises a higher concentration of reproxalap, or a pharmaceutically acceptable salt thereof, than an ophthalmic solution administered in a maintenance phase. In some embodiments, the ophthalmic solution administered in an initiation phase or an exacerbation phase and the ophthalmic solution administered in a maintenance phase, comprises reproxalap, or a pharmaceutically acceptable salt, at a concentration selected from the group consisting of about 0.5% w/v, 0.45% w/v, 0.4% w/v, 0.35% w/v, 0.3% w/v, 0.25% w/v, 0.2% w/v, 0.15% w/v, and 0.1% w/v.

In some embodiments, an ophthalmic solution of about 0.5% w/v reproxalap is administered in an initiation phase or exacerbation phase, and less than 0.5% w/v reproxalap administered in a maintenance phase. In some embodiments, an ophthalmic solution of about 0.4% w/v, 0.35% w/v, 0.3% w/v, 0.25% w/v, 0.2% w/v, 0.15% w/v or 0.1% w/v reproxalap is administered in the maintenance phase.

In some embodiments, an ophthalmic solution of about 0.5% w/v to about 0.4% reproxalap is administered in an initiation phase or exacerbation phase, and less than 0.4% w/v reproxalap administered in a maintenance phase. In some embodiments, an ophthalmic solution of about 0.35% w/v, 0.3% w/v, 0.25% w/v, 0.2% w/v, 0.15% w/v or 0.1% w/v reproxalap is administered in the maintenance phase.

In some embodiments, an ophthalmic solution of about 0.5% w/v to about 0.3% reproxalap is administered in an initiation phase or exacerbation phase, and less than 0.3% w/v reproxalap administered in a maintenance phase. In some embodiments, an ophthalmic solution of about 0.25% w/v, 0.2% w/v, 0.15% w/v or 0.1% w/v reproxalap is administered in the maintenance phase.

In some embodiments, an ophthalmic solution of about 0.4% w/v to about 0.3% reproxalap is administered in an initiation phase or exacerbation phase, and less than 0.3% w/v reproxalap administered in a maintenance phase. In some embodiments, an ophthalmic solution of about 0.25% w/v, 0.2% w/v, 0.15% w/v or 0.1% w/v reproxalap is administered in the maintenance phase.

In some embodiments, an ophthalmic solution of about 0.3% w/v to about 0.2% reproxalap (e.g., 0.3%, 0.25%, or 0.2% w/v) is administered in an initiation phase or exacerbation phase, and 0.25% w/v or less reproxalap administered in a maintenance phase. In some embodiments, an ophthalmic solution of about 0.25% w/v, 0.2% w/v, 0.15% w/v or 0.1% w/v reproxalap is administered in the maintenance phase.

In some embodiments, an ophthalmic solution of the invention is topically administered more frequently per day in an initiation phase and/or an exacerbation phase than in a maintenance phase. In some embodiments, an ophthalmic solution of the invention is topically administered five times a day in an initiation phase, followed by four, three, two, one times a day, or as needed in a maintenance phase. In some embodiments, an ophthalmic solution of the invention is topically administered four times a day (QID) in an initiation phase or exacerbation phase, followed by three times a day (TID), two times a day (BID), once a day (QD), or as needed (PRN) in a maintenance phase. In some embodiments, an ophthalmic solution of the invention is topically administered three times a day (TID) in an initiation phase or exacerbation phase, followed by two times a day (BID) or once per day (QD), or as needed (PRN) in a maintenance phase. In some embodiments, an ophthalmic solution of the invention is topically administered two times a day (BID) in an initiation phase or exacerbation phase, followed by once daily (QD) or as needed (PRN) in a maintenance phase.

In some embodiments, an ophthalmic solution of the invention used for the initiation phase and the maintenance phase has the same concentration of reproxalap (e.g., 0.5%, 0.4% 0.3%, 0.25%, or 0.2% w/v) when the frequency of administration is varied for the initiation phase and the maintenance phase.

In some embodiments, an ophthalmic solution administered in an initiation phase or exacerbation phase is at a higher reproxalap concentration and higher administration frequency than an ophthalmic solution administered in a maintenance phase.

In some embodiments, the present invention provides a method for treating allergic conjunctivitis in a subject, comprising topically administering to the subject an ophthalmic solution comprising about 0.4% w/v reproxalap, or a pharmaceutically acceptable salt thereof, and a pharmaceutically acceptable excipient, wherein the ophthalmic solution is administered at a higher strength in an initiation phase or exacerbation phase followed by a lower strength in a maintenance phase, wherein each of the initiation phase, exacerbation phase, and maintenance phase is as described herein.

In some embodiments, a multiple phase treatment cycle can include an initiation phase or exacerbation phase of up to 1, up to 2, up to 3, up to 4 up to 6, up to 8, or up to 12 weeks with an ophthalmic solution comprising about 0.5%, 0.4% or 0.35% w/v, 0.25% (e.g., 0.5% to 0.35% w/v) reproxalap, or a pharmaceutically acceptable salt thereof, followed by a maintenance phase. In some embodiments, an ophthalmic solution comprising about 0.5%, 0.4% or 0.35% w/v, 0.25% (e.g., 0.5% to 0.35% w/v) reproxalap, or a pharmaceutically acceptable salt thereof, is administered four times a day (QID) in an initiation phase or exacerbation phase followed by three times a day (TID), two times a day (BID), or once per day (QD) in the maintenance phase. In some embodiments, an ophthalmic solution comprising about 0.5%, 0.4% or 0.35% w/v, 0.25% (e.g., 0.5% to 0.35% w/v) reproxalap, or a pharmaceutically acceptable salt thereof, is administered three times a day (TID) in an initiation phase or exacerbation phase followed by two times a day (BID) or once per day (QD) in the maintenance phase.

In some embodiments, an ophthalmic solution comprising about 0.4%, 0.35% or 0.3% w/v (e.g., 0.4% to 0.3% w/v) reproxalap, or a pharmaceutically acceptable salt thereof, is administered four times a day (QID) in an initiation phase or exacerbation phase followed by three times a day (TID), two times a day (BID), or once per day (QD) in the maintenance phase. In some embodiments, an ophthalmic solution comprising about 0.4%, 0.35% or 0.3% w/v (e.g., 0.4% to 0.3% w/v) reproxalap, or a pharmaceutically acceptable salt thereof, is administered three times a day (TID) in an initiation phase or exacerbation phase followed by two times a day (BID) or once per day (QD) in the maintenance phase.

In some embodiments, an ophthalmic solution comprising about 0.3%, 0.25% or 0.2% w/v (e.g., 0.3% to 0.2% w/v) reproxalap, or a pharmaceutically acceptable salt thereof, is administered four times a day (QID) in an initiation phase or exacerbation phase followed by three times a day (TID), two times a day (BID), or once per day (QD) in the maintenance phase. In some embodiments, an ophthalmic solution comprising about 0.3%, 0.25% or 0.2% w/v (e.g., 0.3% to 0.2% w/v) reproxalap, or a pharmaceutically acceptable salt thereof, is administered three times a day (TID) in an initiation phase or exacerbation phase followed by two times a day (BID) or once per day (QD) in the maintenance phase.

In some embodiments, the present invention provides a method for treating allergic conjunctivitis in a subject, comprising topically administering to the subject an ophthalmic solution comprising 0.35% to 0.45% w/v reproxalap, or a pharmaceutically acceptable salt thereof, and a pharmaceutically acceptable excipient, wherein the ophthalmic solution is administered at a higher strength in an initiation phase or exacerbation phase followed by a lower strength in a maintenance phase, wherein each of the initiation phase, exacerbation phase and maintenance phase is as described herein. In some embodiments, a multiple phase treatment cycle of an ophthalmic solution comprising 0.35% to 0.45% w/v reproxalap, or a pharmaceutically acceptable salt thereof, is up to 12 weeks. In some embodiments, an ophthalmic solution comprising 0.35% to 0.45% w/v reproxalap, or a pharmaceutically acceptable salt thereof, is administered four times a day (QID) in an initiation phase or exacerbation phase followed by three times a day (TID), two times a day (BID), or once per day (QD) in maintenance phase. In some embodiments, an ophthalmic solution comprising 0.35%-0.45% w/v reproxalap, or a pharmaceutically acceptable salt thereof, is administered three times a day (TID) in an initiation phase or exacerbation phase followed by two times a day (BID) or once per day (QD) in maintenance phase.

In some embodiments, the treatment regimen with an ophthalmic solution of the invention provides a statistically significant reduction in the ocular itch scale of a patient population suffering from allergic conjunctivitis. In some embodiments, the treatment regimen with the ophthalmic solution of the invention provides a statistically significant ($p<0.05$) reduction by at least 1 point in the ocular itch scale of a patient population suffering from allergic conjunctivitis. In some embodiments, the treatment regimen with the ophthalmic solution of the invention provides a statistically significant (p<0.05) reduction by at least 2 points in the ocular itch scale of a patient population suffering from allergic conjunctivitis. Ocular Itch Scale 0 (no itch) to 4 (incapacitating itch).

In some embodiments, the present invention provides a method for treating certain subjects with allergic conjunctivitis. In some embodiments, a subject with allergic conjunctivitis is 18 years or older. In some embodiments, a subject with allergic conjunctivitis has a history of allergic conjunctivitis for at least six months prior to receiving the treatment of the invention. In some embodiments, a subject with allergic conjunctivitis has a history of use or desire to use eye drops for symptoms within six months prior to receiving the treatment of the invention.

In some embodiments, the present invention provides a method for treating a subject with allergic conjunctivitis, comprising identifying subjects satisfying one or more of the following criteria for at least one eye, prior to receiving the treatment of the invention (for example, a screening performed at about one and/or two weeks before receiving the treatment):
- having a Schirmer's Test score of ≤10 mm and ≥1 mm;
- having a tear film break-up time (TFBUT©)≤5 seconds;
- having a corneal fluorescein staining score of ≥2 in at least one region (e.g., inferior, superior, or central);
- having a sum corneal fluorescein staining score of ≥4 based on the sum of the inferior, superior, and central regions; and
- having a total Lissamine green conjunctival score of ≥2 based on the sum of the temporal and nasal regions.

In some embodiments, the present invention provides a method for treating a subject with allergic conjunctivitis comprising a screening to exclude subjects having one or more of the following conditions for at least one eye, prior to receiving the treatment of the invention:
- having any clinically significant slit lamp findings that may include active blepharitis, meibomian gland dysfunction (MGD), lid margin inflammation, or active ocular allergies that may require therapeutic treatment;
- having an ongoing ocular infection (bacterial, viral, or fungal), or active ocular inflammation;
- having previously had laser-assisted in situ keratomileusis (LASIK) surgery within the last 12 months;
- having any planned ocular and/or lid surgeries over the study period or any ocular surgery within six months; and
- having a known allergy and/or sensitivity to an ophthalmic solution of the invention or its components.

As described herein, an ophthalmic solution of the invention can achieve an increased efficacy in subjects with allergic conjunctivitis. Accordingly, in some embodiments, the present invention provides a method for treating a subject with allergic conjunctivitis comprising topically administering to the subject an ophthalmic solution of the invention.

In some embodiments, the present invention provides a method for treating allergic conjunctivitis in a subject, comprising topically administering to the subject an ophthalmic solution described herein, wherein the ophthalmic solution is administered three times a day (TID), two times a day (BID), or once per day (QD). In some embodiments, an ophthalmic solution comprising about 0.25% w/v reproxalap, or a pharmaceutically acceptable salt thereof, is administered three times a day (TID). In some embodiments, an ophthalmic solution comprising about 0.25% w/v reproxalap, or a pharmaceutically acceptable salt thereof, is administered two times a day (BID). In some embodiments, an ophthalmic solution comprising about 0.25% w/v reproxalap, or a pharmaceutically acceptable salt thereof, is administered once daily (QD).

For topical ophthalmic administration, each administration comprises one or more aliquots of the composition (e.g., ophthalmic solution). In some embodiments, the aliquot administered in an estimated volume, for example an applied drop using a dropper or a squeeze vial. In some embodiments, one or more drops, two drops, three drops, up to 4 drops are topically applied to an eye or to each of both eyes at each administration. In some embodiments, each administration comprises sequential administration, for example, a first administration of one or more aliquots (e.g., one or more drops), a first time period for allowing absorption of the composition, followed by a second administration of one or more aliquots (e.g., one or more drops). In some embodiments, one drop provides a single dose of the ophthalmic solution. In some embodiments, the volume for topical administration is about 25 uL to about 75 uL. In some embodiment, the volume for topical administration is about 30 uL to about 60 uL. In some embodiments, the volume for topical administration is about 50 uL. In some embodiments, the volume of one drop of an ophthalmic solution of the invention is approximately 30 uL to 50 uL. In some embodiments, the volume of one drop of an ophthalmic solution of the invention is approximately 50 uL.

In some embodiments, a presently disclosed ophthalmic solution is co-administered with an additional therapeutic agent. In some embodiments, the additional therapeutic agent is an agent disclosed in WO2017147617 or WO2017196881, each of which is hereby incorporated by reference in its entirety. In some embodiments, the additional therapeutic agent is an antihistamine, mast cell inhibitor, or anti-inflammatory agent. Exemplary antihistamines include, among others, levocabastine, olopatadine, and ketotifen fumarate. In some embodiments, the anti-inflammatory agent is a steroid, non-steroidal anti-inflammatory compound, anti-metabolite, immunosuppressive antibiotic, alkylating agent, or an anti-inflammatory cytokine antibody. Exemplary steroidal compounds include, among others, cortisol, cortisone, prednisone, prednisolone (e.g., prednisolone acetate), methylprednisone, triamcinolone, betamethasone, dexamethasone and a prodrug thereof. Exemplary non-steroidal anti-inflammatory compounds include, among others, acetylsalicylic acid, diflunisal, salsalate, ibuprofen, dexibuprofen, naioxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, phenylbutazone, mefenamic acid, meclofenamic acid, flufenamic acid, tolfenamic acid, and celecoxib. Exemplary antimetabolites include, among others, azathioprine, mercaptopurine, leflunomide, mycophenolic acid, and mycophenolate mofetil, and methotrexate. Exemplary anti-inflammatory antibiotics include, among others, cyclosporine, tacrolimus, rapamycin, and derivatives thereof. Exemplary anti-inflammatory antibodies, include among others, antibodies targeting an inflammatory cytokine, such as antibodies against TNFα. IL-1, IL-4, IL-5, and IL-17.

In another aspect, further provided herein are methods for assessing the safety, efficacy, comparability, or bioequivalence of an aldehyde trapping compound for treating allergic conjunctivitis using an EEC chamber protocol. In some embodiments, a method for assessing the safety, efficacy, comparability or bioequivalence of an aldehyde trapping compound for treating allergic conjunctivitis, comprising placing a test subject in an EEC chamber, providing one or more test allergens, administering a test aldehyde trapping compound or a composition thereof, and assessing severity of symptoms of allergic conjunctivitis. In some embodiments, the symptoms for assessing severity of allergic conjunctivitis includes, among others, one or more of ocular itch, ocular tearing, and conjunctival redness. In some embodiments, the test aldehyde trapping compound or a composition thereof is administered prior to and/or at start of or after exposure of the test subjects to the allergen. In some embodiments, the method is used to assess the comparability or bioequivalence of ophthalmic compositions containing 0.25% w/v or 0.5% w/v of reproxalap.

EXAMPLES

The following examples are intended to illustrate the invention and are not to be construed as being limitations thereon. Reproxalap can be synthesized as reported previously, for example, in WO 2006/127945, the entire content of which is incorporated herein by reference.

Abbreviations
CAE: controlled adverse environment
GMP: Good Manufacturing Practice
ICH: International Council for Harmonization of Technical Requirements for Pharmaceuticals for Human Use
OD: right eye
OS: left eye
OU: both eyes
PRN: as needed
QD: once daily
QID: Four times daily
QS: as much as will suffice Example 1. A Multi-Center, Double-Masked, Randomized, Parallel-Group, Vehicle-Controlled, Phase 3 Clinical Trial to Assess the Safety and Efficacy of Reproxalap Ophthalmic Solutions (0.25% and 0.5%) Compared to Vehicle in the Conjunctival Allergen Challenge (Ora-CAC®) Model of Acute Allergic Conjunctivitis A double-masked, randomized, vehicle-controlled, multi-center, parallel-group conjunctival allergen challenge Phase 3 trial assessed the efficacy and safety of 0.25% and 0.5% concentrations of reproxalap topical ophthalmic solutions compared to vehicle in 318 patients (approximately 100 per arm) with seasonal allergic conjunctivitis. The primary efficacy endpoint was the evaluation of ocular itch score (0 to 4 scale) area under the curve from 10 to 60 minutes after allergen challenge, and the key secondary endpoint was two-point responder rate, a measure of clinical relevance.

The primary objective for the study was statistically significant improvement vs. vehicle ($p<0.0001$ and $p=0.0025$, respectively) on primary endpoint of ocular itch score area under the curve from 10-60 minutes after allergen challenge.

The secondary objective for the study was statistically significant improvement vs. vehicle ($p=0.0005$ and $p=0.0169$, respectively) on key secondary responder analysis of two-point improvement in ocular itch score (0-4 scale).

Figure 2:
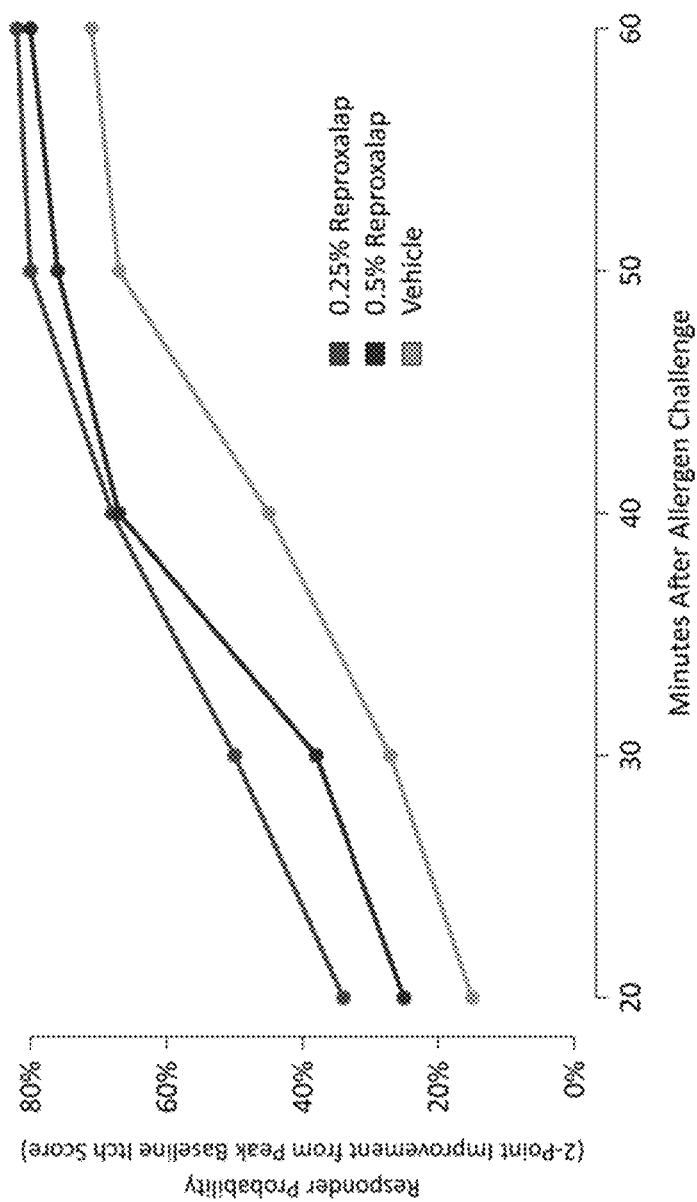
FIG. 2 depicts the probability of a two-point response in ocular itch score over time after an allergen challenge. For both concentrations of reproxalap, the results were statistically superior to vehicle in achieving the result. p=0.0005 for 0.25% reproxalap; p=0.0169 for 0.5% reproxalap.
Figure 3:
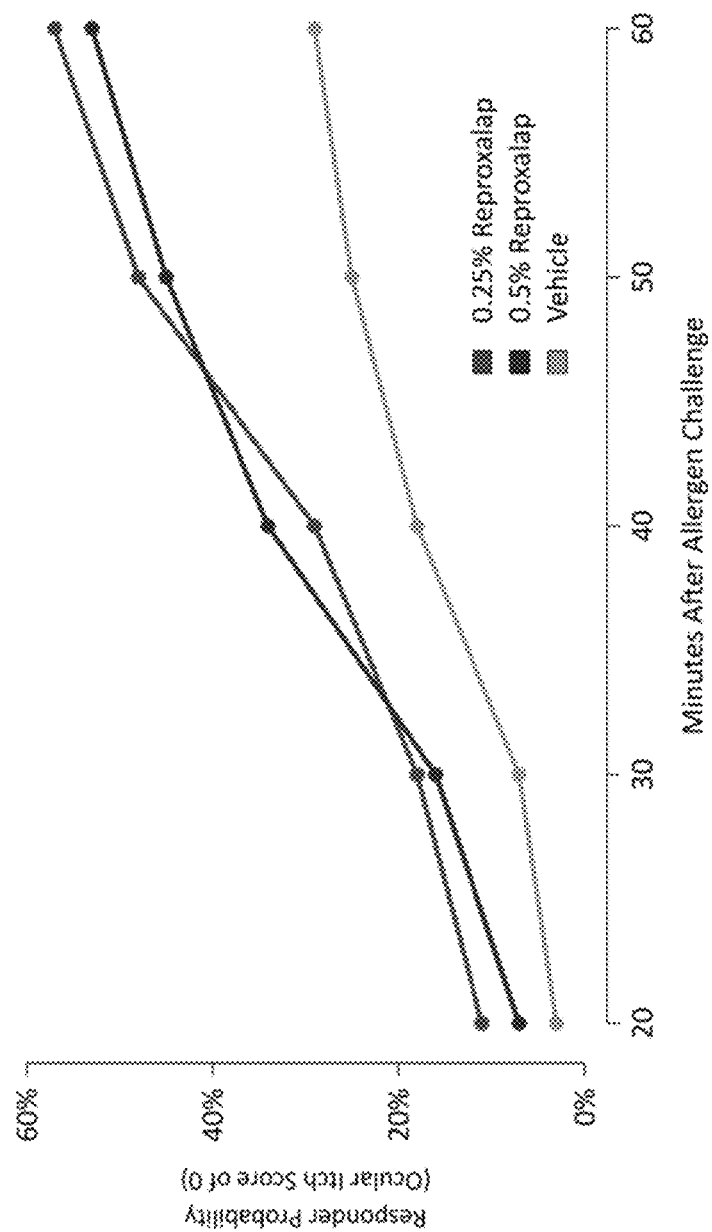
FIG. 3 depicts the probability of an ocular itch score of 0 (therapeutic cure) over time after an allergen challenge. For both concentrations of reproxalap, the results were statistically superior to vehicle in achieving complete reduction of ocular itch. p=0.0006 for 0.25% reproxalap; p=0.0045 for 0.5% reproxalap.

Relative to patients treated with vehicle, patients treated with 0.25% and 0.5% reproxalap demonstrated statistically significant reduction in ocular itching ($p<0.0001$ and $p=0.0025$, respectively; FIG. 1), as assessed by area under the ocular itch score curve. Two-point responder rates for 0.25% and 0.5% reproxalap were statistically greater than that of vehicle-treated patients ($p=0.0005$ and $p=0.0169$, respectively; FIGS. 2 and 3), confirming the clinical relevance of the observed primary endpoint improvements. Both concentrations of reproxalap exhibited an anti-inflammatory profile that is distinct from standard-of-care antihistamine therapy and supports a differentiated mechanism of action for the treatment of allergic conjunctivitis.

No adverse events were observed other than mild, transient instillation site irritation, consistent with prior reproxalap clinical trials.

No observed findings were observed on the following safety assessments: visual acuity (ETDRS chart), intraocular pressure (contact tonometry), slit lamp biomicroscopy, and dilated fundoscopy.

Duration

This trial consisted of four (4) office visits (Screening Visit, Visit 1, Visit 2, and Visit 3) over a period of approximately three to nine (3-9) weeks.

Screening Period: Screening was approximately 3-9 weeks in duration. At Visit 1, subjects underwent an ocular allergen challenge titration using an allergen that elicited a positive reaction via skin testing. Subjects with a positive reaction post-CAC underwent a confirmation CAC at Visit 2 with the same allergen qualified during Visit 1.

Treatment Period: Treatment begins at Visit 3 after subjects are randomized. At this visit, subjects receive an in-office dose of the treatment.

Inclusion Criteria

Each subject must:

be at least 18 years of age of either gender and any race;
have a positive history of ocular allergies and a positive skin test reaction to a seasonal allergen (grasses, ragweed, and/or trees) as confirmed by an allergic skin test at the Screening Visit or within the past 24 months;
be able and willing to avoid all disallowed medications for the appropriate washout period and during the trial;
be able and willing to discontinue wearing contact lenses for at least 72 hours prior to Visit 1 and during the trial period;
have a calculated visual acuity of 0.7 log MAR or better in each eye as measured using an ETDRS chart;
agree to have urine pregnancy testing (for women considered capable of becoming pregnant, including all females who have experienced menarche and have not experienced menopause [as defined by amenorrhea for greater than 12 consecutive months] or have not undergone successful surgical sterilization [hysterectomy, bilateral tubal ligation, or bilateral oophorectomy]) performed at screening and exit visit; not be lactating; and agree to use a medically acceptable form of birth control throughout the trial duration;
have a positive bilateral CAC reaction ($\geq 2.5$ ocular itching and $\geq 2$ conjunctival redness) within 10 ($\pm 2$) minutes of instillation of the last titration of allergen at Visit 1; and
have a positive bilateral CAC reaction ($\geq 2.5$ ocular itching and $\geq 2$ conjunctival redness) for at least two out of the first three time points following the challenge at Visit 2.

Exclusion Criteria

Each subject may not:

have known contraindications or sensitivities to the use of the investigational product or any of its components;

have any ocular condition that, in the opinion of the investigator, could affect the subject's safety or trial parameters (including but not limited to narrow angle glaucoma, clinically significant blepharitis, follicular conjunctivitis, iritis, pterygium or a diagnosis of dry eye);

have had ocular surgical intervention within three (3) months prior to Visit 1 or during the trial and/or a history of refractive surgery six (6) months prior to Visit 1 or have ocular or systemic surgery planned during the study or within 30 days after;

have a known history of retinal detachment, diabetic retinopathy, or active retinal disease;

have the presence of an active ocular infection (bacterial, viral or fungal), any active uveitis, or positive history of ocular herpes or an ocular herpetic infection at any visit;

use any of the following disallowed medications during the period indicated prior to Visit 1 and during the trial:
72 hours
   systemic or ocular $H_1$ antihistamine, $H_1$ antihistamine/mast cell stabilizers, $H_1$ antihistamine-vasoconstrictor drug combinations
7 days
   decongestants
   monoamine oxidase inhibitors
   all other topical ophthalmic preparations (including artificial tears)
   lid scrubs
   topical prostaglandins or prostaglandin derivatives
   ocular, topical, or systemic nonsteroidal anti-inflammatory drugs (NSAIDs); Baby aspirin (81 mg) is allowed as long as a stable dose has been maintained for at least 30 days prior to Visit 1 and will continue to be maintained for the duration of the trial.
14 days
   inhaled, ocular, topical, or systemic corticosteroids or mast cell stabilizers
45 days
   depo-corticosteroids
2 months
   immunotherapeutic agents (treatment must have been maintained steadily for at least 2 months; neither the immunotherapeutic agent nor its dosage may change during the clinical trial) (Note: Currently marketed over-the-counter anti-allergy eye drops (e.g., anti-histamine/vasoconstrictor combination products) may be administered by trained trial personnel to subjects at the end of Visits 1, 2, and 3, after all evaluations are completed.)

have any significant illness (including, but not limited to, poorly controlled hypertension, poorly controlled diabetes, a history of status asthmaticus, a history of organ transplantation, a history of persistent moderate or severe asthma, a history of moderate to severe allergic asthmatic reactions to any of the trial allergens, any autoimmune disease requiring therapy, or severe cardiovascular disease or arrhythmia) that, at the investigators' discretion, could be expected to interfere with the subject's health or with the trial parameters and/or put the subject at any unnecessary risk;

manifest signs or symptoms of clinically active allergic conjunctivitis in either eye at the start of Visits 1, 2, or 3 (defined as the presence of any itching or >1 [greater than 1] redness in the conjunctival vessel bed);

have a history of glaucoma, ocular hypertension or an intraocular pressure (IOP) that is greater than 24 mmHg at Visit 1;

have used an investigational drug or medical device within 30 days of the trial or be concurrently enrolled in another investigational product trial;

be a female who is currently pregnant, planning a pregnancy, lactating, not using a medically acceptable form of birth control throughout the trial duration, or has a positive urine pregnancy test at Visit 1.

Statistical Analysis

The primary efficacy variable of ocular itch score (scale 0 to 4) area under the curve from 10-60 minutes post-challenge (AUC 10-60) is measured at Visit 3. A generalized linear model containing treatment as a main effect and, if useful, Visit 2 baseline information as one or more covariates, was fit to Visit 3 AUC 10-60 data. The model was used to evaluate two contrasts: a) Reproxalap Ophthalmic Solution 0.5% mean AUC 10-60 vs. Vehicle Ophthalmic Solution mean AUC 10-60, and b) Reproxalap Ophthalmic Solution 0.25% mean AUC 10-60 vs. Vehicle Ophthalmic Solution mean AUC 10-60. The primary efficacy analyses was conducted on the intent-to-treat (ITT) population.

The Key Secondary Endpoint (intended to be used for US NDA approval) of within-subject two-point response (i.e., two-point reduction from Visit 2 5-minute post-CAC itch score at 20 through 60 minutes post-CAC Visit 3) was evaluated using a GEE containing treatment, post-CAC Visit 3 measurement time, the treatment×time interaction, and, if useful, Visit 2 baseline information as one or more covariates. The model was used to evaluate the odds ratio of Reproxalap Ophthalmic Solution 0.5% vs. Vehicle Ophthalmic Solution, and Reproxalap Ophthalmic Solution 0.25% vs. Vehicle Ophthalmic Solution across combined Visit 3 post-CAC time points for the ITT population utilizing an assumed covariance matrix within the GEE to accommodate missing data. Significance levels for these contrasts was adjusted for multiplicity using the Hochberg procedure to avoid false discovery (Reference: FDA, Multiple Endpoints in Clinical Trials, Draft Guidance for Industry, January 2017).

Phase 3 AC Formulation: 0.5% Reproxalap Ophthalmic Solution A

Composition of 0.5% Reproxalap Ophthalmic Solution A

| Component | Amount (% w/v) | Grade |
|---|---|---|
| ADX-102 (reproxalap) | 0.5% | GMP |
| Sulfobutylether-beta-cyclodextrin (SBECD) | 9.5% | USP |
| Sodium phosphate, dibasic, anhydrous | 0.083% | USP |
| Sodium phosphate, monobasic, monohydrate | 0.017% | USP |
| Sodium hydroxide or Hydrochloric acid | pH adjustment | USP/NF |
| Sterile Water for Injection (WFI) | Dilute to volume | USP |

Phase 3 AC Formulation: 0.5% Reproxalap Ophthalmic Solution B

Composition of 0.5% Reproxalap Ophthalmic Solution B

| Component | Amount (% w/v) | Grade |
|---|---|---|
| ADX-102 (reproxalap) | 0.5% | GMP |
| Sulfobutylether-beta-cyclodextrin (SBECD) | 9.5% | USP |
| Sodium hydroxide or Hydrochloric acid | pH adjustment | USP/NF |
| Sterile Water for Injection (WFI) | Dilute to volume | USP |

Phase 3 AC Formulation: 0.25% Reproxalap Ophthalmic Solution A

Composition of 0.25% Reproxalap Ophthalmic Solution A

| Component | Amount (% w/v) | Grade |
|---|---|---|
| ADX-102 (reproxalap) | 0.25% | GMP |
| Sulfobutylether-beta-cyclodextrin (SBECD) | 7.0% | USP |
| Sodium phosphate, dibasic, anhydrous | 0.083% | USP |
| Sodium phosphate, monobasic, monohydrate | 0.017% | USP |
| Sodium chloride | 0.24% | USP |
| Sodium chloride | Tonicity adjustment | USP |
| Sodium hydroxide or Hydrochloric acid | pH adjustment | USP/NF |
| Sterile Water for Injection (WFI) | Dilute to volume | USP |

Phase 3 AC Formulation: 0.25% Reproxalap Ophthalmic Solution (Basic)

Composition of 0.25% Reproxalap Ophthalmic Solution B

| Component | Amount (% w/v) | Grade |
|---|---|---|
| ADX-102 (reproxalap) | 0.25% | GMP |
| Sulfobutylether-beta-cyclodextrin (SBECD) | 7.0% | USP |
| Sodium chloride | Tonicity adjustment | USP |
| Sodium hydroxide or Hydrochloric acid | pH adjustment | USP/NF |
| Sterile Water for Injection (WFI) | Dilute to volume | USP |

In some embodiments, a basic ophthalmic solution is provided above. Additional excipients may be optionally added to the basic ophthalmic solution.

Phase 3 AC Composition of Vehicle Ophthalmic Solution

Composition of Vehicle Ophthalmic Solution

| Component | Amount (% w/v) | Grade |
|---|---|---|
| Sodium phosphate, dibasic, anhydrous | 0.083% | USP |
| Sodium phosphate, monobasic, monohydrate | 0.017% | USP |
| Sodium Chloride | 0.9% | USP |
| Sodium hydroxide or Hydrochloric acid | pH adjustment | USP/NF |
| Sterile Water for Injection (WFI) | Dilute to volume | USP |

Generally, the vehicle used is the same as the AC formulations but without the reproxalap. In some embodiments, where the AC formulation do not include sodium phosphate and/or sodium chloride, the vehicle formulation do not include the sodium phosphate and/or the sodium chloride.

Example 2: A Clinical Trial Evaluating Reproxalap Ophthalmic Solutions in Subjects with Seasonal Allergic Conjunctivitis Using the Environmental Exposure Chamber (EEC)

The clinical trial evaluated the feasibility of using the Environmental Exposure Chamber (EEC) to assess the activity of Reproxalap Ophthalmic Solutions (0.25% and 0.5%) in an allergic conjunctivitis population.

The study assessed the safety, tolerability, and pharmacodynamic activity of Reproxalap ophthalmic solutions (0.25% and 0.5%) compared to vehicle ophthalmic solution in the treatment of seasonal allergic conjunctivitis in subjects allergic to ragweed using the EEC with exposure to airborne ragweed pollen. The EEC is a chamber, e.g., a room, that provides reproducible challenges with controlled levels with airborne allergen and control of environmental factors, such as humidity and temperature (Devillier et al., Allergy, 2011, 66(2):163-9; Goldstein et al., Eye & Contact Lens, 2015, 41(3):145-155; Jacobs et al., J Allergy Clin Immunol., 2012, 130:122-7). The EEC chambers have been used for Phase 3 studies to provide real-life conditions for natural allergen exposure (Pfaar et al., Allergy, 2017, 73(Suppl 104):5-23). It allows for better assessment of the dose response, onset of action, and magnitude of treatment effects, and further provides low variability in outcomes and reduced confounding factors—further controlled in this study with restrictions in timing for EEC assessments relative to work schedule Inclusion/Exclusion Criteria included, among others, the following:
  A history of moderate-to-severe ragweed-induced allergic conjunctivitis
  Positive skin prick test to ragweed pollen within the past year of the Medical Screening Visit
  Have a positive bilateral CAC reaction to ragweed allergen (≥2 ocular itching and redness scores) within 10 minutes of instillation of the last titration of allergen at Visit 2
  Have signs and symptoms of allergic conjunctivitis in both eyes (≥1 ocular itching and redness) for ≥4 days of the 1 week artificial tears run-in period prior to Visit 3.

The EEC clinical research facility was designed with the capacity and control mechanisms to expose participants to airborne ragweed pollen grains and maintains target temperature and relative humidity throughout. The EEC has 100% fresh HEPA-filtered clean air to which commercially obtained air dried, non-defatted short ragweed (*Ambrosia artemesiifolia*) pollen (Greer Laboratories, Lenoir, N.C.) were introduced and circulated throughout the room with tight humidity and temperature controls as described previously (Ronborg et al., Allergy, 1996, 51(2):82-88). Airborne ragweed pollen counts were maintained at 3500±500 grains per cubic meter by continuous monitoring and feedback regulation of the pollen emission measured. The controlled pollen challenge, over time, allowed evaluation of subject responses at any time-point throughout the challenge process.

Patients were subject to medical screening and EEC screening, as highlighted above for inclusion/exclusion criteria. A skin prick test for a standard panel of test allergens was conducted including cat, dust, ragweed, grass or tree pollen. Results must be positive (i.e., a wheal 3 mm greater than the negative control) for at least one test allergen and must include ragweed in order to proceed to the Screening EEC Visit.

For EEC treatment sessions, patients were randomized into three treatment groups: (A) treatment with Reprolaxap 0.25% ophthalmic solution, (B) treatment with 0.5% ophthalmic solution, and (C) vehicle treatment. In the EEC treatment sessions, dosing was 5 min prior to entry into the chamber, and 95 min post entry into the chamber. The patients were in the EEC for approximately 215 min. Following exit from the EEC, patients were monitored for ocular itching and tearing for up to about 60 min. Staff assessed conjunctival redness were assessed up to about 60 min following exit from the chamber. The patients were subject to three sessions in the EEC chamber, where each EEC sessions were separated by approximately a two-week washout period to ensure adequate elimination of responses caused by allergen exposure in the EEC and allow the recuperation of mast cells.

For subject-reported symptoms of ocular itching, a standard 9 point (i.e., 0-4 with 0.5 unit increments) and a standard VAS scale (0-100 mm) were employed. For subject rated ocular tearing, a 4-point scale (0-3) was employed. For staff-assessed grading of conjunctival redness, a standard 9-point (i.e., 0-4 with 0.5 unit increments) was employed.

Figure 4:
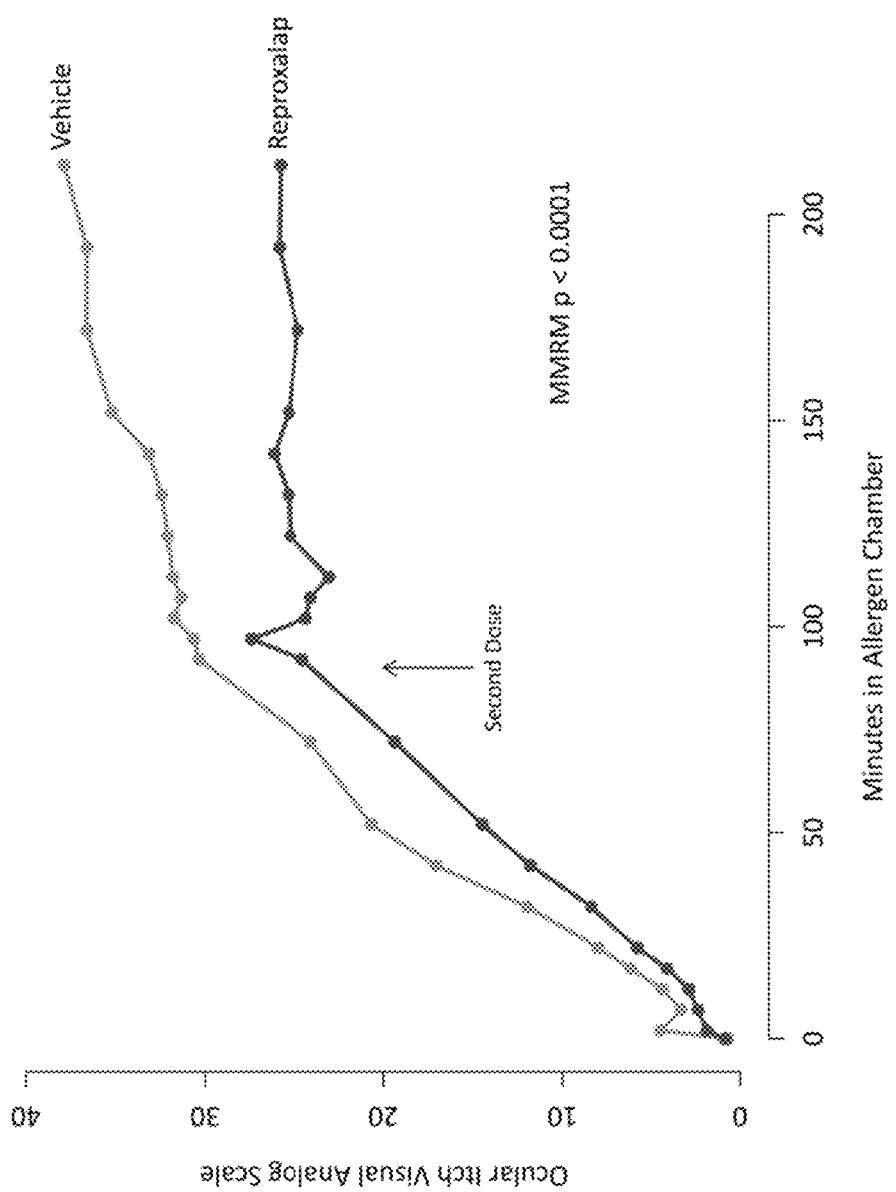
FIG. 4 depicts ocular itch score (0-100) during 200 minutes of allergen exposure in a group chamber model of allergic conjunctivitis. The results are shown for 0.25% w/v Reproxalap administered at 5 min prior to and 95 min after exposure to an allergen (ragweed). Treatment with Reproxalap shows statistically significant reduction in ocular itch vs. vehicle for more than 3 hrs of exposure to the allergen.

FIG. 4 shows the ocular itch score (0-100) during 200 minutes of allergen exposure in the EEC. Treatment with 0.25% w/v Reproxalap shows statistically significant reduction in ocular itch vs. vehicle for more than 3 hrs of exposure to allergen.

Figure 5:
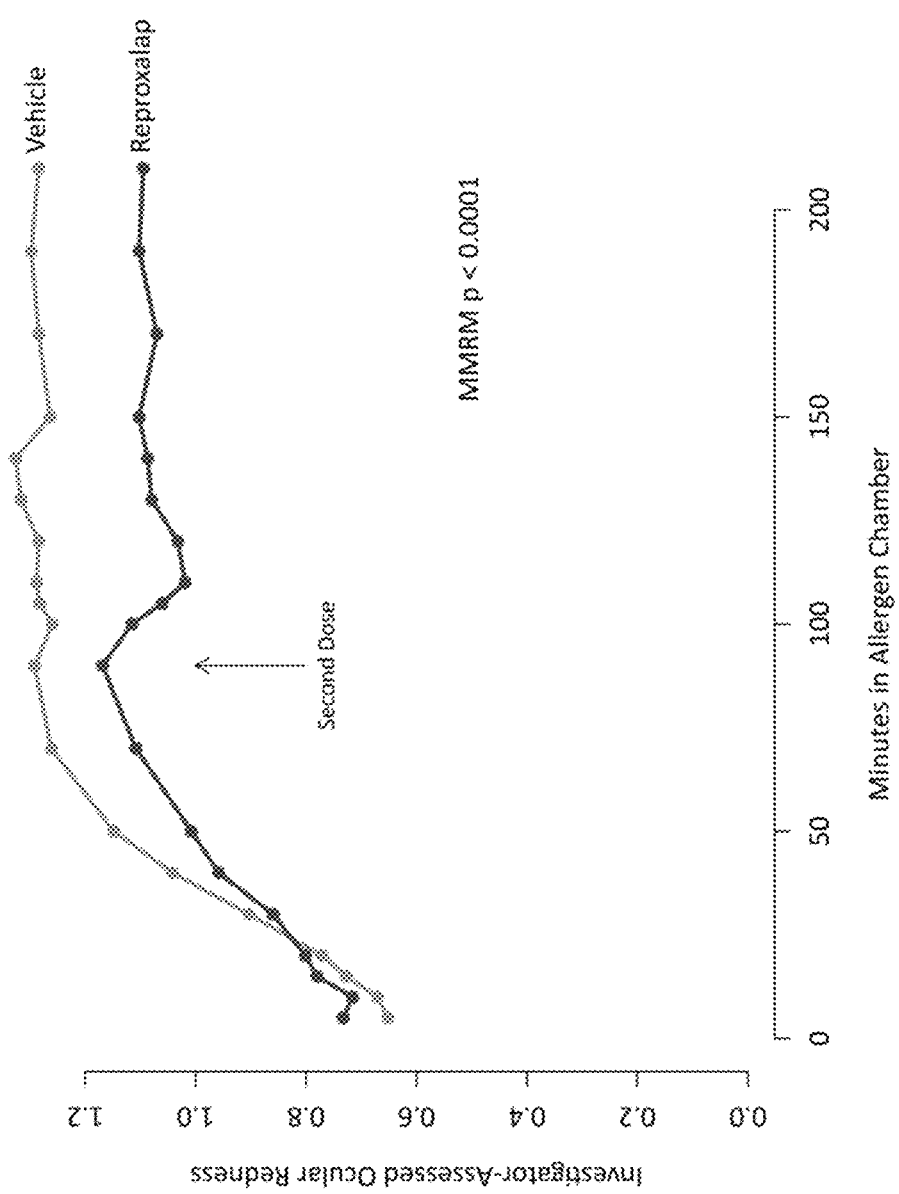
FIG. 5 depicts ocular redness score (0-4) during 200 minutes of allergen exposure in a group chamber model of allergic conjunctivitis. The results are shown for 0.25% w/v Reproxalap administered at 5 min prior to and 95 min after exposure to allergen (ragweed). Treatment with Reproxalap shows statistically significant reduction in ocular redness vs. vehicle for more than 3 hrs of exposure to allergen.

FIG. 5 shows the ocular redness score (0-4) during 200 minutes of allergen exposure in the EEC. Treatment with 0.25% w/v Reproxalap shows statistically significant reduction in ocular redness vs. vehicle for more than 3 hrs of exposure to allergen.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. A method of treating allergic conjunctivitis in a subject, comprising topically administering to an eye of a subject in need thereof a therapeutically effective amount of an ophthalmic solution comprising reproxalap, or a pharmaceutically acceptable salt thereof, and a pharmaceutically acceptable excipient, wherein the concentration of reproxalap, or a pharmaceutically acceptable salt thereof, is about 0.25% w/v, and the pharmaceutically acceptable excipient is about 7% w/v of sulfobutylether β-cyclodextrin (SBECD), or a pharmaceutically acceptable salt thereof.

2. The method of claim 1, wherein the ophthalmic solution further comprises a tonicity agent and a buffer.

3. The method of claim 1, wherein the administering is prior to an expected or certain exposure of the subject to an eye allergen.

4. The method of claim 3, wherein the administering is up to 3.5 h prior to the expected or certain exposure to the eye allergen.

5. The method of claim 3, wherein the ophthalmic solution is administered up to four times, up to five times, up to six times, up to seven times, or up to eight times prior to the expected or certain exposure to an eye allergen.

6. The method of claim 1, wherein the subject for treatment has a history of being afflicted with allergic conjunctivitis and/or has a positive skin test for one or more eye allergens.

7. The method of claim 1, wherein the administering is at or after exposure of the subject to an eye allergen, or at or after onset of symptoms of allergic conjunctivitis.

8. The method of claim 7, wherein the administering is at or after onset of symptoms of allergic conjunctivitis.

9. The method of claim 7, wherein the ophthalmic solution is administered up to twelve times a day, up to ten times a day, up to eight times a day, up to six times a day, up to five times a day, up to four times a day, up to three times a day, up to two times a day, once a day, or as needed at or after exposure of the subject to an eye allergen, or at or after onset of symptoms of allergic conjunctivitis.

10. The method of claim 9, wherein the ophthalmic solution is administered twelve times a day, ten times a day, eight times a day, six times a day, five times a day, four times a day (QID), three times a day (TID), two times a day (BID), once a day (QD), or as needed (PRN).

11. The method of claim 7, wherein the ophthalmic solution is administered twelve times a day, ten times a day, eight times a day, six times a day, four times a day (QID), three times a day (TID), two times a day (BID), or once a day (QD), followed by administration as needed (PRN).

12. The method of claim 1, wherein the treating comprises: a first treatment phase comprising administering the ophthalmic solution prior to an expected or certain exposure of the subject to an eye allergen; and a second treatment phase comprising administering the ophthalmic solution at or after exposure of the subject to an eye allergen, or at or after onset of symptoms of allergic conjunctivitis.

13. The method of claim 12, wherein the first treatment phase comprises administering the ophthalmic solution 3.5 h or less prior to the expected or certain exposure to the eye allergen.

14. The method of claim 12, wherein the first treatment phase comprises administering the ophthalmic solution one time, two times, three times, or four times prior to the expected or certain exposure to an eye allergen.

15. The method of claim 12, wherein the second treatment phase is at or after onset of symptoms of allergic conjunctivitis.

16. The method of claim 12, wherein the second treatment phase comprises administering the ophthalmic solution eight times a day, seven times a day, six times a day, five times a day, four times a day (QID), three times a day (TID), two times a day (BID), once a day (QD), or as needed (PRN).

17. The method of claim 12, wherein the second treatment phase comprises administering the ophthalmic solution eight times a day, seven times a day, six times a day, five times a day, four times a day (QID), three times a day (TID), two times a day (BID), or once a day (QD), followed by administration as needed (PRN).

18. The method of claim 1, wherein the treatment includes an initiation phase, an exacerbation phase and/or a maintenance phase.

19. The method of claim 18, wherein the initiation phase or exacerbation phrase comprises administering the ophthalmic solution five or four times a day (QID).

20. The method of claim 18, wherein the maintenance phase comprises administering the ophthalmic solution four times a day (QID), three times a day (TID), two times a day (BID), once per day (QD), or as needed (PRN).

21. The method of claim 20, wherein the maintenance phase comprises administering the ophthalmic solution two times a day (BID).

22. The method of claim 1, wherein after administration to the subject, the ophthalmic solution provides a statistically significant reduction in the ocular itch scale of the patient as compared to no treatment or vehicle treatment.

23. The method of claim 22, wherein the reduction in the ocular itch score is by at least 1 point.

\* \* \* \* \*